(12) United States Patent
Yifat et al.

(10) Patent No.: US 11,744,529 B2
(45) Date of Patent: Sep. 5, 2023

(54) SUPPLEMENTARY COLLISION DETECTION AND PREVENTION SYSTEM FOR A MEDICAL IMAGER

(71) Applicant: Radiaction Ltd, Tel Aviv (IL)

(72) Inventors: Jonathan Yifat, Ramat Hasharon (IL); Yossi Bar, Haifa (IL); Amir Belson, Savyon (IL)

(73) Assignee: Radiaction Ltd.

( * ) Notice: Subject to any disclaimer, the term of this patent is extended or adjusted under 35 U.S.C. 154(b) by 501 days.

(21) Appl. No.: 16/731,471

(22) Filed: Dec. 31, 2019

(65) Prior Publication Data

US 2020/0205753 A1 Jul. 2, 2020

Related U.S. Application Data

(60) Provisional application No. 62/787,644, filed on Jan. 2, 2019.

(51) Int. Cl.
*A61B 6/10* (2006.01)
*A61B 6/00* (2006.01)

(52) U.S. Cl.
CPC .............. *A61B 6/102* (2013.01); *A61B 6/107* (2013.01); *A61B 6/4441* (2013.01); *A61B 6/4405* (2013.01); *A61B 6/547* (2013.01); *A61B 2562/0219* (2013.01); *A61B 2562/0247* (2013.01); *A61B 2562/0257* (2013.01); *A61B 2562/0261* (2013.01); *A61B 2562/0271* (2013.01)

(58) Field of Classification Search
CPC .... A61B 2562/0219; A61B 2562/0247; A61B 2562/0257; A61B 2562/0261; A61B 2562/0271; A61B 6/102; A61B 6/107; A61B 6/4405; A61B 6/4441; A61B 6/547
See application file for complete search history.

(56) References Cited

U.S. PATENT DOCUMENTS

| | | | |
|---|---|---|---|
| 5,570,770 A * | 11/1996 | Baaten | A61B 6/102 477/186 |
| 6,325,538 B1 * | 12/2001 | Heesch | A61B 6/4452 250/517.1 |
| 6,830,375 B2 | 12/2004 | Deshpande | |
| 7,029,175 B2 | 4/2006 | Karaus et al. | |

(Continued)

FOREIGN PATENT DOCUMENTS

| | | | |
|---|---|---|---|
| DE | 102013214222 A1 | 1/2015 | |
| DE | 102014215448 B3 * | 12/2015 | ............... A61B 6/02 |
| WO | WO-2017083437 A1 | 5/2017 | |

OTHER PUBLICATIONS

English translation of DE-102014215448 (Year: 2014).*

(Continued)

*Primary Examiner* — Dani Fox
*Assistant Examiner* — Soorena Kefayati
(74) *Attorney, Agent, or Firm* — WILSON SONSINI GOODRICH & ROSATI

(57) ABSTRACT

The present invention relates to a collision detection and prevention system for medical X-ray equipment, in particular a supplementary system that augments an existing safety system, which is useful when the X-ray equipment includes an auxiliary apparatus, such as a radiation shield, which may interfere with the existing collision detection and prevention system.

30 Claims, 13 Drawing Sheets

(56) References Cited

U.S. PATENT DOCUMENTS

| | | | |
|---|---|---|---|
| 7,837,385 B2 | 11/2010 | Klingenbeck-Regn | |
| 8,113,713 B2 | 2/2012 | Belson et al. | |
| 8,439,564 B2 | 5/2013 | Belson et al. | |
| 8,767,920 B2 | 7/2014 | Spahn | |
| 9,370,331 B2* | 6/2016 | Belson | A61B 6/4423 |
| 9,907,519 B2 | 3/2018 | Belson et al. | |
| 2004/0042587 A1* | 3/2004 | Deshpande | A61B 6/4482 378/198 |
| 2004/0257744 A1* | 12/2004 | Bushko | A61B 6/102 361/179 |
| 2006/0097734 A1* | 5/2006 | Roziere | G01B 7/023 324/662 |
| 2007/0086570 A1* | 4/2007 | Spahn | A61B 6/4452 378/117 |
| 2007/0242805 A1* | 10/2007 | Somers | A61B 6/102 427/79 |
| 2007/0269012 A1* | 11/2007 | Somers | A61B 6/102 378/117 |
| 2008/0258929 A1* | 10/2008 | Maschke | A61B 6/547 340/686.1 |
| 2008/0304626 A1* | 12/2008 | Camus | A61B 6/4441 378/209 |
| 2009/0232282 A1* | 9/2009 | Belson | A61B 6/4441 378/209 |
| 2014/0275998 A1 | 9/2014 | Eichler et al. | |
| 2014/0334608 A1* | 11/2014 | Mulzer | A61B 6/04 378/207 |
| 2015/0117615 A1* | 4/2015 | Dirauf | H10N 35/101 378/117 |
| 2015/0128727 A1* | 5/2015 | Sattler | A61B 6/102 73/862.625 |
| 2015/0305694 A1* | 10/2015 | Sakata | A61B 6/0407 378/204 |
| 2015/0359505 A1* | 12/2015 | Hoshino | A61B 6/102 600/407 |
| 2016/0143600 A1* | 5/2016 | Schmidt | A61B 6/4441 378/204 |
| 2016/0193731 A1* | 7/2016 | Sattler | A61B 34/30 901/9 |
| 2016/0345929 A1* | 12/2016 | Azizian | B25J 9/1676 |
| 2017/0220709 A1* | 8/2017 | Wan | A61N 5/1048 |
| 2018/0000431 A1 | 1/2018 | Roth et al. | |
| 2018/0168525 A1 | 6/2018 | Belson et al. | |
| 2018/0214100 A1* | 8/2018 | Kumar | A61B 6/4429 |
| 2018/0249972 A1 | 9/2018 | Yifat et al. | |
| 2018/0289342 A1* | 10/2018 | Chandwadkar | A61B 5/6802 |

OTHER PUBLICATIONS

EP19908003.7 Extended Search Report dated Sep. 1, 2022.
International Search Report and Written Opinion for PCT/US2019/069158 dated Jun. 5, 2020.

* cited by examiner

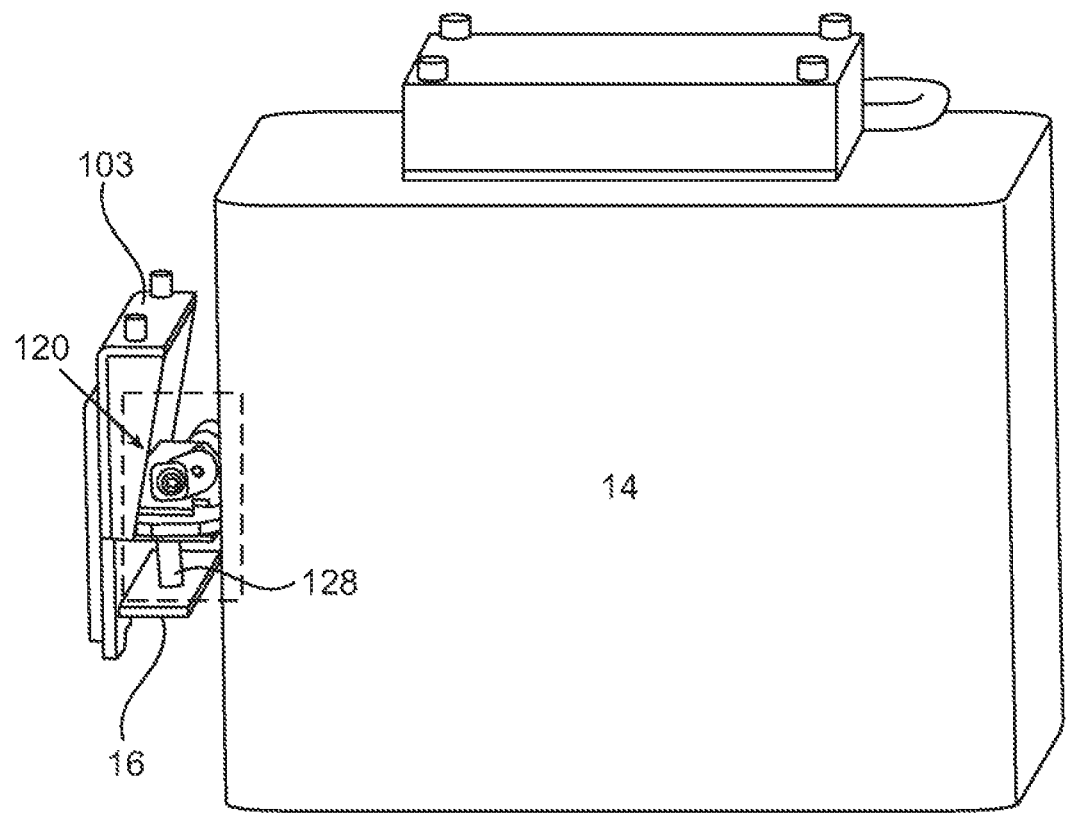
FIG. 7A
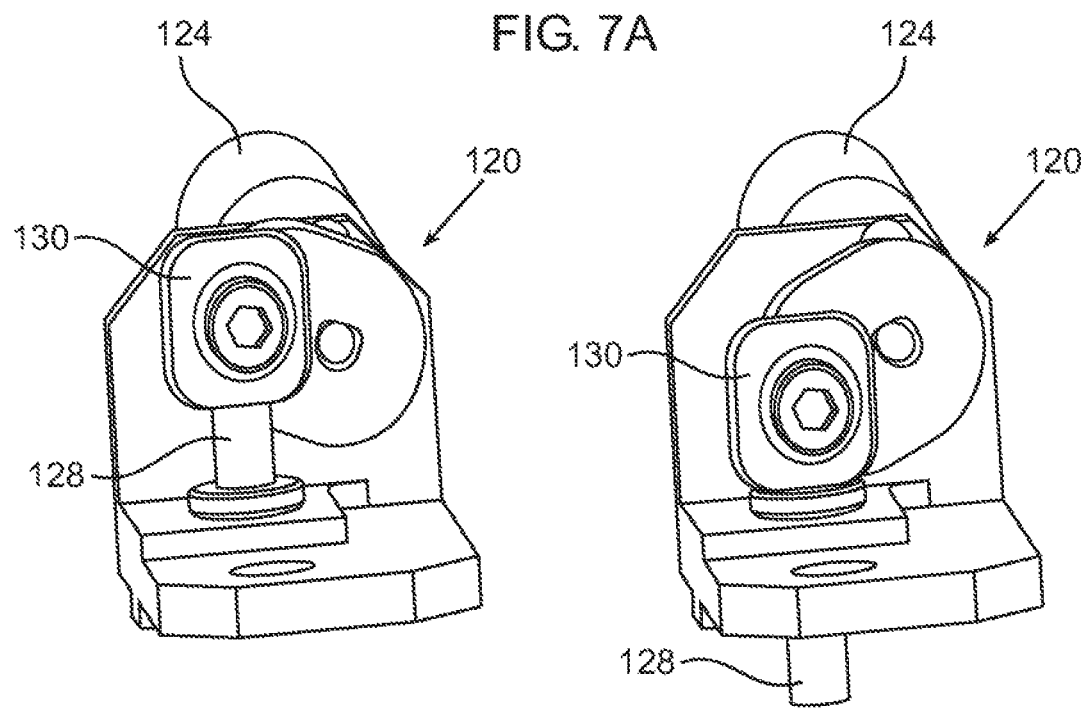
FIG. 7B
FIG. 7C

SUPPLEMENTARY COLLISION DETECTION AND PREVENTION SYSTEM FOR A MEDICAL IMAGER

CROSS REFERENCE TO RELATED APPLICATIONS

This application claims priority from U.S. Provisional No. 62/787,644, filed Jan. 2, 2019, the entire contents of which is incorporated herein by reference.

FIELD OF THE INVENTION

The present invention relates to a collision detection and prevention system for medical X-ray equipment, in particular a supplementary system that augments an existing safety system, which is useful when the X-ray equipment includes an auxiliary apparatus, such as a radiation shield, which may interfere with the existing collision detection and prevention system.

BACKGROUND OF THE INVENTION

Medical equipment, in particular X-ray equipment and X-ray fluoroscopy systems, which may be in motion during operation, may include an anti-collision mechanism. The anti-collision mechanism typically includes a plurality of proximity sensors for the safe operation and positioning of a movable radiation imaging component (e.g. an X-ray source and/or a detector of an X-ray "C-arm") and can be important for protecting patients as well as protecting expensive medical equipment.

For safe positioning and movement of movable radiation imaging medical equipment (e.g. X-ray equipment), a proximity/collision detection means may be disposed on or around portions of the imaging equipment to prevent collision with a patient and/or other objects such as an X-ray table or a procedure table.

However, in some circumstances, in particular when an auxiliary apparatus such as a radiation shield is installed, the native collision detection means may be blocked or partially blocked and thus is rendered ineffective or limited.

Exemplary related disclosures include U.S. Pat. No. 8,767,920 (Siemens); U.S. Pat. No. 7,029,175 (GE Medical); U.S. Pat. No. 7,837,385 (Siemens); U.S. Pat. No. 6,830,375 (GE Medical); U.S. Pat. No. 8,439,564 (Radguard); U.S. Pat. No. 8,113,713 (Radguard); U.S. Pat. No. 9,907,519 (Radiaction); and US 2018/249972 (Radiaction), all of which are incorporated by reference in their entirety as if fully set forth herein.

SUMMARY OF THE INVENTION

The present disclosure relates to a system for and method of allowing safe and effective X-ray imaging, in particular in the case when a native proximity/collision means of the imaging equipment is rendered at least partially ineffective due to an auxiliary apparatus, for example a radiation shield. This is achieved by providing a proximity and collision detection system which serves to backup, provide supplemental, and/or improve the existing (native) collision prevention means of X-ray imaging equipment (e.g., a C-arm).

The present supplementary collision detection and prevention system provides for collision avoidance between moving parts of a medical X-ray device and a patient or other object (hereinafter used interchangeably with the term "entity").

The supplementary system includes one or more sensors, which can be configured to provide layers of protection, in particular one or more combinations of (a) at least one proximity and/or contact sensor, which may include distance measurement sensors to determine proximity; (b) at least one inertial and/or gyroscopic sensor to determine movement, rate of movement toward an entity and/or direction of movement; (c) at least one operator detection sensor, for example to determine if an operator is actively operating or intends to operate the C-arm (e.g. in a manner that may lead to a collision with the patient or patient table); and (d) at least one electrical current sensor to measure electrical current consumption in one or more units of the X-ray system (e.g., C-arm's motor) and determine operation thereof that may lead to collision The present system is configured to be added to existing medical X-ray equipment and to interface, mechanically and/or electronically, with the native collision prevention means of the X-ray equipment (e.g. with a C-arm thereof). Alternatively or additionally, the sensor(s) is/are added to a an add-on system (e.g., a radiation shielding system) of an X-ray system.

An aspect of the invention pertains to a collision detection and prevention system which can be coupled onto a piece of X-ray equipment and includes one or more collision sensors; and/or one or more inertial sensors; and or/or one or more electrical current sensors; and/or one or more operation detection sensor and a trigger or trigger mechanism that triggers or actuates a native anti-collision mechanism/means of the X-ray equipment. The trigger/trigger mechanism may be mechanical or electrical (including wireless).

An aspect of the invention pertains to an add-on system (for example, for a radiation shielding apparatus) of an X-ray device that includes at least one supplemental sensor, including one of or a combination of: one or more proximity and/or collision sensors; one or more inertial motion/gyroscopic sensor; one or more operator detection sensor; and one or more electrical current sensor; and a trigger mechanism that triggers or activates a native anti-collision mechanism/means of the X-ray system, or a portion thereof (e.g., a native collision sensor of the X-ray system).

An aspect of the invention pertains to a supplementary system of additional collision sensors in accordance with the disclosure herein above.

Avoiding the collision may include ceasing movement of a component (e.g. radiation shield) and/or distancing the component from the entity (patient, object or the like) based upon proximity of a sensor within a pre-determined distance to the entity or contact with the entity; or dangerous movement of the component, for example, as determined by an inertial sensor; or an operator action, as determined by an operator detection sensor.

The trigger mechanism may include a mechanical trigger configured to activate a native proximity or contact sensor of the X-ray equipment.

The mechanical trigger may include a trigger motor or other actuator configured to contact or apply pressure to a native contact sensor or be proximal to a native proximity sensor of the native anti-collision mechanism of the X-ray equipment.

The trigger mechanism may include an electrical trigger that employs an electrical/electronic connection with the anti-collision means of the X-ray equipment and/or with a radiation shield to activate the X-ray equipment's native collision safety system.

The supplemental sensor may be a contact sensor. The supplemental sensor may be a proximity sensor. The supplemental sensor may be a pressure sensor. The supplemental sensor may be a strain sensor. The supplemental sensor may be an infrared sensor. The supplemental sensor may be an ultrasonic sensor. The supplemental sensor may be a laser sensor. The supplemental sensor may be a radio frequency sensor. The supplemental sensor may be an electro-optic sensor (e.g. a camera) which may be configured to identify an activity by an operator, such as touching an operator handle. The supplemental sensor may be a thermal or temperature sensor (e.g. including or constituted by a thermocouple). The supplemental sensor may an electrical current sensor that measures an electrical current flowing in an electrical wire.

In one or more embodiments, the trigger mechanism and/or sensors is/are coupled to an interface. In one or more embodiments, the interface is disposed in one or more locations around and/or on the X-ray system. In one or more embodiments, the interface is disposed in one or more locations around and/or on an X-ray radiation shielding system of the X-ray equipment. In one or more embodiments, the collision detection system activates a native X-ray anti-collision means upon detection of a possible collision with an object or patient (entity). In one or more embodiments, the collision detection system ceases to activate a native X-ray equipment's anti-collision means when proximity or contact of a sensor to a patient or object is no longer detected. In one or more embodiments, the collision detection system further includes an alarm unit that operates to alert medical staff upon detection of a possible collision with an entity.

An aspect of the invention pertains to a supplementary collision detection and prevention system for use in combination with medical imaging equipment which comprises a native anti-collision mechanism having native sensors and an add-on system that limits the functionality of the native anti-collision mechanism, the supplementary collision detection and prevention system comprising:

a plurality of supplemental sensors being any one of a proximity sensor and/or contact sensor, and/or an inertial motion sensor, and/or an operator detection sensor, and/or an electrical current sensor configured to facilitate prevention or protection from collision with an entity; and an interface configured to receive communication from at least one of the plurality of supplemental sensors and to transmit a signal that actuates an anti-collision operation of the medical imaging equipment, and/or actuates the add-on system thereof, to avoid or mitigate a collision.

In one or more embodiments, the interface communicates with the native anti-collision mechanism of the medical imaging equipment, and/or with a trigger mechanism of the system that actuates at least one of the native sensors.

In one or more embodiments, the system further comprising a command controller configured to actuate an anti-collision operation of the add-on system or of the medical imaging equipment.

In one or more embodiments, the add-on system is a radiation blocking shield and wherein at least one of the supplemental sensors is associated with the radiation blocking shield.

In one or more embodiments, the radiation blocking shield extends from a radiation shield support base and wherein the support base includes one or more of the plurality of supplemental sensors.

In one or more embodiments, the radiation shield is a retractable shield that is configured to retract in response to the signal.

In one or more embodiments, at least one of the plurality of supplemental sensors is selected from the group consisting of: a pressure sensor; a strain sensor; an infrared sensor; an ultrasonic sensor; an ultrasound sensor; a laser sensor; a radio frequency sensor; an electro-optic sensor; and a thermal sensor, of any combination thereof.

In one or more embodiments, the electrical motor-current sensor is configured to measure electrical current consumption in one more units of the medical imaging equipment and detect operation thereof that may lead to collision with the entity.

In one or more embodiments, the operator detection sensor is configured to detect an activity by an operator that can lead to collision with the entity.

In one or more embodiments, the operator detection sensor is associated with a foot pedal or an operation control panel of the medical imaging equipment.

In one or more embodiments, the operator detection sensor is selected from the group consisting of a proximity sensor; a contact sensor; an infra-red sensor; an optic sensor; and a combination thereof.

In one or more embodiments, the inertial motion sensor is an accelerometer or a gyroscopic sensor.

In one or more embodiments, the inertial motion sensor is configured to detect movement of a moving part of the medical imaging equipment.

In one or more embodiments, the entity is a patient, a patient table, an operator or a piece of medical imaging equipment.

An aspect of the invention pertains to a radiation shielding apparatus comprising:

at least one radiation blocking shield positioned around an X-ray source or an X-ray detector of a medical imaging equipment; wherein the medical imaging equipment comprises a native anti-collision detection mechanism including at least one native sensor; and a supplementary collision detection and prevention system configured to avoid collision of an entity with the X-ray source, X-ray detector, and/or X-ray radiation shield, the supplementary collision detection and prevention system comprising:

a plurality of supplemental sensors being any one of a proximity sensor and/or contact sensor, and/or an inertial motion sensor, and/or an operator detection sensor, and/or an electrical current sensor configured to facilitate prevention or protection from collision with the entity; and a command controller configured to receive communication from the supplemental sensors and mechanically and/or electrically actuate an anti-collision operation of the medical imaging equipment and/or radiation shielding apparatus, to avoid or mitigate a collision.

In one or more embodiments, the apparatus further comprising a mechanical trigger configured to actuate at least one of the native sensors in response to the mechanical and/or electrical operation, thereby activating the native anti-collision mechanism of the medical imaging equipment.

In one or more embodiments, the electrical anti-collision operation includes an electrical trigger that actuates the native anti-collision mechanism.

In one or more embodiments, at least one of the supplemental sensors is associated with the radiation blocking shield.

In one or more embodiments, the radiation blocking shield extends from a radiation shield support base and wherein the support base includes one or more of the supplemental sensors.

In one or more embodiments, the radiation shield or a portion thereof is configured to retract in response to the electrical an anti-collision operation.

In one or more embodiments, at least one of the supplemental sensors is a sensor selected from the group consisting of: a pressure sensor; a strain sensor; an infrared sensor; an ultrasonic sensor; an ultrasound sensor; a laser sensor; a radio frequency sensor; an electro-optic sensor; and a thermal sensor, or any combination thereof.

In one or more embodiments, the electrical current sensor is configured to measure electrical current consumption in one more units of the medical imaging equipment and detect operation thereof that may lead to collision with the entity.

In one or more embodiments, the operator detection sensor is configured to detect an activity by an operator that can lead to collision with the entity.

In one or more embodiments, the operator detection sensor is associated with a foot pedal or an operation control panel of the medical imaging equipment.

In one or more embodiments, the operator detection sensor is selected from the group consisting of a proximity sensor; a contact sensor; an infra-red sensor; an optic sensor; and a combination thereof.

In one or more embodiments, the inertial motion sensor is a gyroscopic sensor.

In one or more embodiments, the inertial motion sensor is disposed on the radiation blocking shield, and/or the X-ray source and/or the X-ray detector.

In one or more embodiments, the entity is a patient, a patient table, an operator or a piece of C-arm equipment.

The present invention further pertains to a method of detecting and/or avoiding a collision of a moveable portion of a piece of medical imaging equipment which comprises a native anti-collision mechanism and a radiation blocking shield or an auxiliary apparatus that limits the functionality of native anti-collision sensors of the native anti-collision mechanism, the method comprising:

sensing proximity and/or contact with an entity, and/or detecting an operator action, and/or sensing an electrical current of the medical imaging equipment, and/or the radiation blocking shield, and/or the auxiliary apparatus;

communicating the sensing to a command controller of the radiation blocking shield or auxiliary apparatus; and mechanically and/or electrically actuating an anti-collision operation of the medical imaging equipment, radiation blocking shield, and/or auxiliary apparatus, to avoid or mitigate a collision.

In one or more embodiments, the method further comprising mechanically triggering at least one of the native sensors in response to the mechanical and/or electrical operation.

In one or more embodiments, the method further comprising transmitting a signal to an electrical trigger that actuates the native anti-collision mechanism.

In one or more embodiments, the step of actuating the anti-collision operation comprises retracting the radiation blocking shield.

In one or more embodiments, the method further comprising stopping or slowing the moveable portion of the medical imaging equipment.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. Particulars shown are by way of example and for purposes of illustrative discussion of embodiments of the invention. In this regard, the description taken with the drawings makes apparent to those skilled in the art how embodiments of the invention may be practiced.

In the drawings:

FIG. 7A is a perspective schematic illustration of another exemplary mechanical trigger mechanism of the present system.

FIGS. 7B and 7C are enlarged schematic perspective views of the mechanical trigger mechanism of FIG. 7A, in a non-triggering position (FIG. 7B) and a triggering position (FIG. 7C).

It should be appreciated that for simplicity and clarity of illustration, elements shown in the figures are not necessarily drawn to scale. Further, where considered appropriate, reference numerals have been repeated among the figures to indicate similar elements.

DETAILED DESCRIPTION OF THE INVENTION

It is understood that the invention is not limited to the particular methodology, devices, items or products etc., described herein, as these may vary as the skilled artisan will recognize. It is also to be understood that the terminology used herein is used for the purpose of describing particular embodiments only and is not intended to limit the scope of the invention. The following exemplary embodiments may be described in the context of exemplary proximity and/or collision detection system for ease of description and understanding. However, the invention is not limited to the specifically described products and methods and may be adapted to various applications without departing from the overall scope of the invention. All ranges disclosed herein include the endpoints. The use of the term "or" shall be construed to mean "and/or" unless the specific context indicates otherwise.

The present supplementary collision detection and prevention system may be implemented as a multi-layered safety system that includes a plurality of safety mechanisms that can work simultaneously with parallel redundancy between layers. The purpose of these safety mechanisms is to ensure the safety of the patient and the smooth and safe operation of a C-arm or the like, when used in conjunction with an auxiliary apparatus, such as a radiation protection shield(s).

An aspect of some embodiments of the current invention relates to an additional or supplementary collision detection and prevention system for medical X-ray equipment or associated device. In some embodiments, a sensor is added to an existing medical X-ray device or a portion thereof and/or the sensor is integrated into the X-ray collision prevention system. In some embodiments, a sensor is added to an add-on system of the X-ray system. Exemplary add-on systems include, without limitation, radiation shielding apparatuses, the teachings of which are provided in the following disclosures: U.S. Pat. Nos. 8,439,564, and 8,113,713, US patent application No. 2018/0168525, International patent application No. WO 2017/083437, and US patent application No.: 2018/0249972, the content of which are incorporated by reference as if fully set forth herein. In some embodiments, a sensor is added to an X-ray radiation shielding system/apparatus of the X-ray system.

Figure 1:
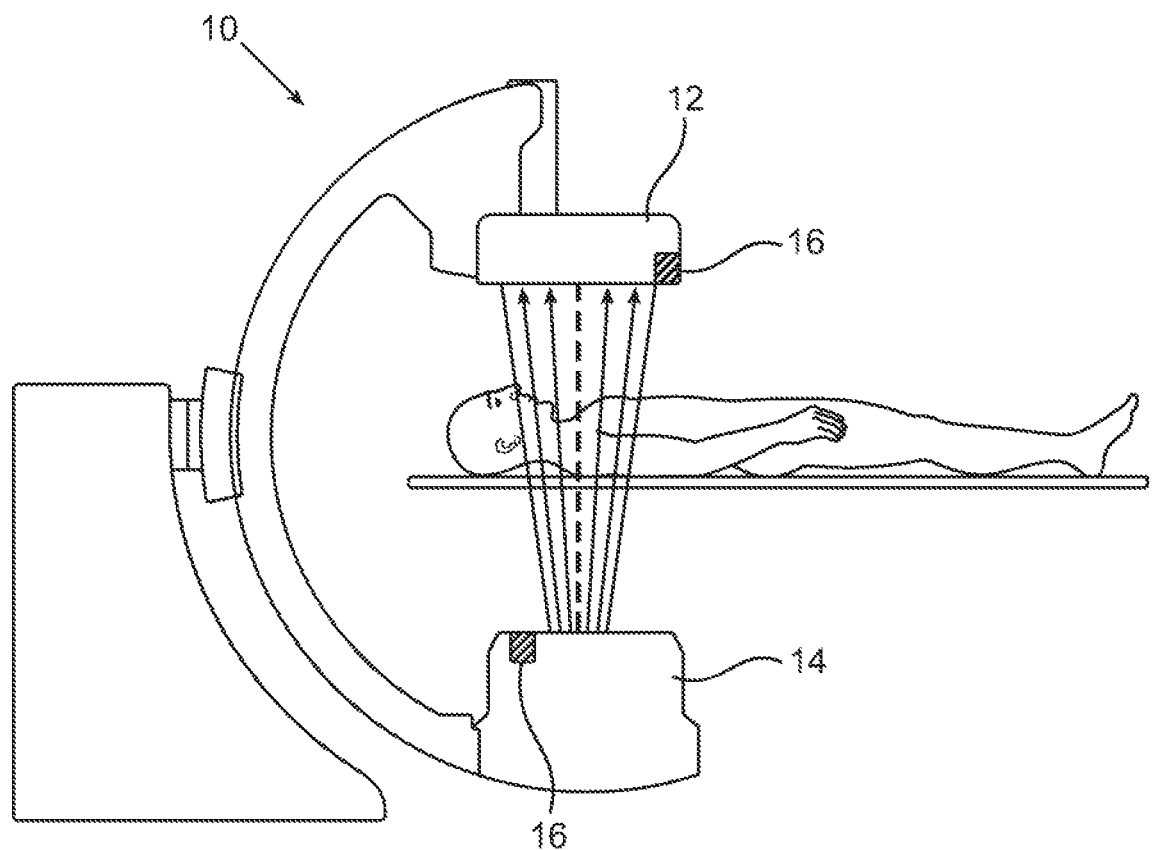
FIG. 1 is a schematic side view of a typical prior art C-arm of an X-ray equipment.

With reference to FIG. 1 (prior art), angiography and fluoroscopy equipment (e.g. a full-sized fixed C-arm or mobile C-arm) often has a mechanism to prevent collisions of the detector/image intensifier and/or the collimator/X-ray source with the patient, table or other objects. This X-ray equipment often employs proximity or contact sensors. When triggered, these sensors may activate a collision prevention or avoidance means (hereinafter "native collision safety means" or "native collision safety mechanism" of the C-arm). For example, the collision prevention means may stop the motion of the C-arm and provide a warning sound and/or visuals (e.g., alarm lights) of such collision, or its imminent occurrence, to the operator.

Some embodiments of the additional or supplementary collision detection and prevention system may provide additional safety and/or collision prevention. For example, additional collision detection may be used in cases where the native collision safety means of the C-arm is inaccessible, inactive and/or does not operate properly. Such cases might occur when the C-arm's collision prevention sensors are obscured by an auxiliary and/or add-on apparatus and/or by other equipment or devices that may interfere. For example, additional collision detection may be used when an add-on system protrudes from the X-ray equipment, or a portion thereof, increasing the area/equipment that requires collision monitoring and protection.

FIG. 1 is an example of a prior art C-arm 10, which is a typical element of X-ray equipment, such as angiography and fluoroscopy equipment. This equipment often includes a mechanism to prevent collisions of the detector 12 (image intensifier) and/or collimator or X-ray source 14 with the patient, table or other equipment/objects (hereinafter "entity"). These anti-collision mechanisms commonly employ proximity and/or contact sensors, which for clarity will be referred to as native sensors 16 (FIG. 1 and FIG. 7A) to activate a collision prevention or avoidance system (existing/native anti-collision means schematically illustrated in FIG. 7A). For example, native anti-collision means may stop the motion of C-arm 10 and provide a warning sound and/or a visual indication upon a collision or imminent collision (proximity beyond a pre-determined threshold), to the operator. In cases where the collision or possible collision is detected at the level of the X-ray detector 12, the detector can be raised upwards to prevent collision with the entity.

Figure 2:
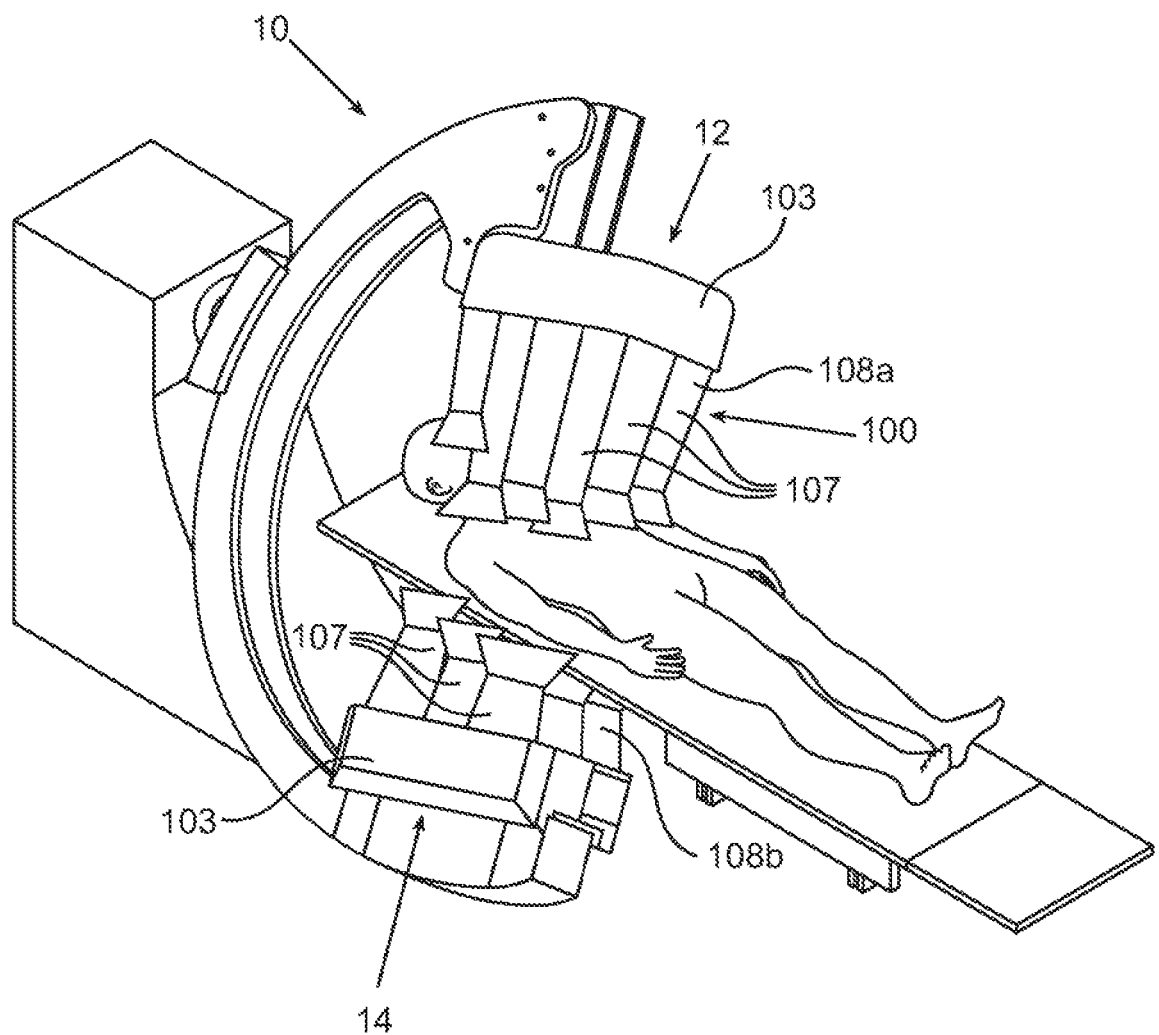
FIG. 2 is a schematic perspective view of a prior art X-ray equipment of FIG. 1 coupled to an auxiliary radiation shielding apparatus.

FIG. 2 shows C-arm 10 with an exemplary auxiliary radiation shielding apparatus 100 which includes an upper radiation shield 108a (interchangeable with "detector's radiation shield") and lower radiation shield 108b (interchangeable with "source radiation shield") that are respectively attached to shield support bases 103 that cover/attached to radiation source detector 12 and radiation source 14. Radiation shields 108a and 108b may be used to protect medical staff or an operator from radiation emitted by the C-arm 10 and/or scattered radiation. Examples of radiation shields are disclosed in US 2018/249972; U.S. Pat. Nos. 8,113,713; and 9,907,519. Such radiation shields, and/or other auxiliary devices, can interfere with (e.g. block) native anti-collision mechanism, in particular the sensors thereof, such as native sensors 16 (FIG. 1). Radiation shields 108a and 108b include a plurality sequentially positioned radiation shield stacks or segments 107, which may be independently controllable to extend or contract to a selected length relative to a patient, or an object such as an X-ray table.

Figure 3:
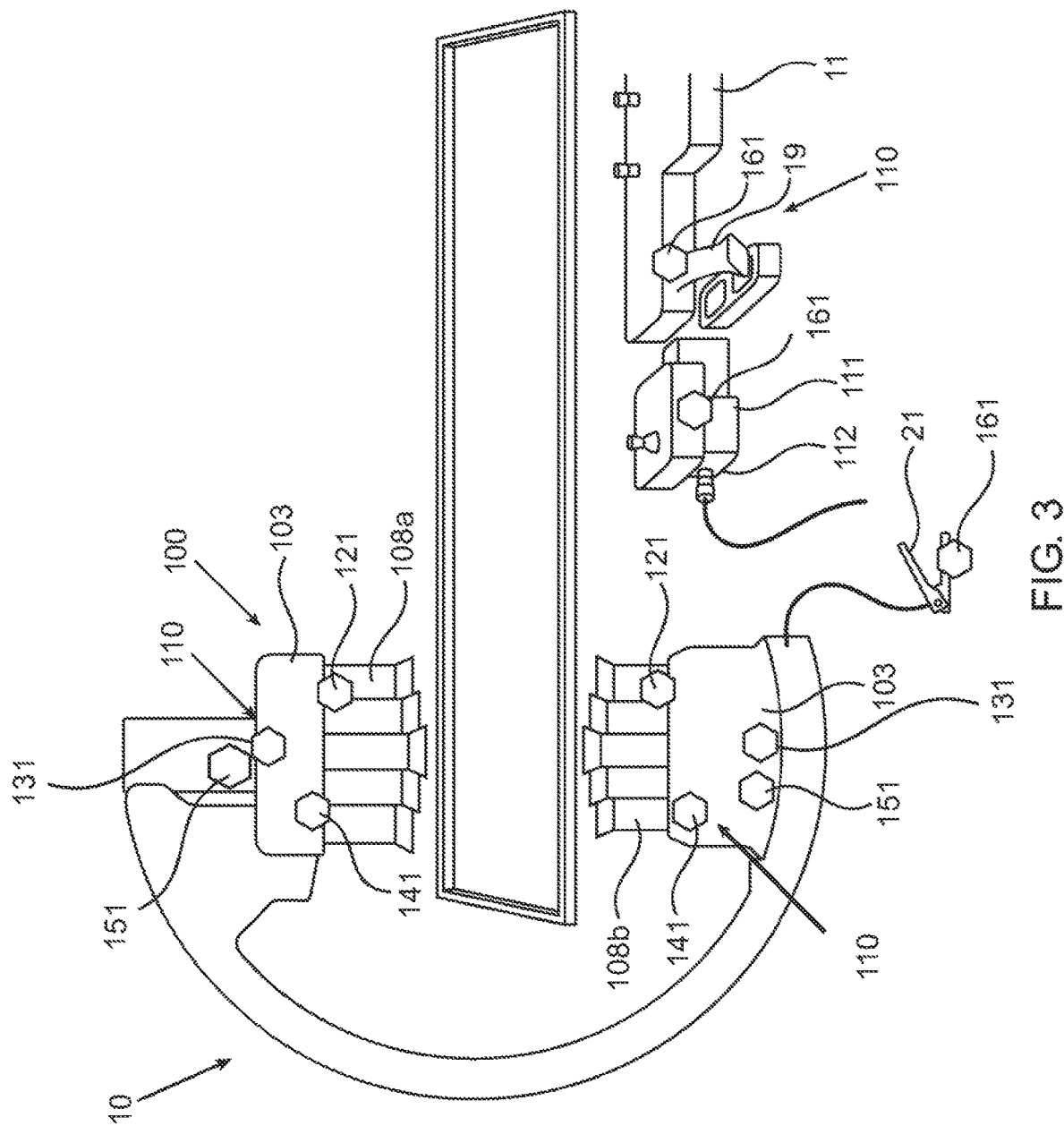
FIG. 3 is a schematic illustration of a supplementary collision detection and prevention system associated with the X-ray equipment and the radiation shielding apparatus of FIG. 2, as well as associated with the operation control panel and elements of the X-ray equipment.

FIG. 3 illustrates an exemplary supplementary collision detection and prevention system 110 of the present invention. System 110 may constitute part of radiation shielding apparatus 100 or may be an individual supplementary system with sensors that can be coupled to an X-ray system (e.g., C-arm 10), a portion thereof, and/or a radiation shielding apparatus (e.g., apparatus 100). System 110 includes one or more supplemental sensors which can cooperate with a command controller 112 thereof (shown located in radiation shield operation control panel 111, but can be provided as an independent component or can be coupled to alternative locations in radiation shielding apparatus 100 or in C-arm 10).

System 110 can include various sensors. Non-limited examples include proximity sensors, optic sensors (e.g. Infra Red, laser optic, etc.), ultrasound sensors, contact sensors, an acceleration sensor, an electromagnetic sensor, electrical current sensors and the like.

System 110 can include one or more sensors working as stand alone or in combination with other sensors or components of the X-ray system 10 or radiation shielding apparatus 100, monitoring various portions of the operating platforms of C-arm 10 or radiation shielding apparatus 100 (e.g. a table mount control panel, a foot pedal, buttons, etc.). The sensors can be fully or partially integrated in these operating platforms such as placing a contact sensor 161 in the foot pedal 21 for sensing the operator pressing the pedal 21. Another sensing option is by using electrical current sensors 151 which are sensors configured to measure electrical current in electrical wires and provide an output of the measured current. Such exemplary sensors may be coupled to one or more designated places in the C-arm unit or portions thereof, such as a C-arm's motor, a C-arm's electrical cabinet (not shown), a portion in the C-arm itself where electrical wires are located, and also at a C-arm's operating platform (e.g., a control panel 11, a foot pedal 21, operation handle 19, etc.). These electrical current sensors detect current flowing in the electrical wires and/or electrical motors, thereby inferring that an operator has activated these functions. In cases in which activation of one or more units of the C-arm may lead to collision, the supplementary anti-collision system may be initiated to avoid collision. Further, electrical current sensors 151 may be coupled to one or more electric wires of a motor of the C-arm and monitor its electrical current.

System 110 includes at least one supplemental sensor which may be proximity sensor 141 and/or a contact sensor 121 which without limitation, may be disposed in one or more locations on radiation shields 108 *a* and 108*b* and/or on shield support bases 103. For example, sensors may be located on the edges or close to edges of the radiation shields 108 *a* and 108*b*.

System 110 may further include one or more electrical current sensors 151, which may be operatively connected to a C-arm motor to indicate current in the motor and thereby detect C-arm motion or imminent collision with an entity. Various alternative locations of the electrical current sensors 151 are contemplated, although not shown, such as in foot pedal 21, in handle 19, etc. to detect operation thereof and avoid or minimize collision in cases where activation of those units of the C-arm may lead to collision.

System 110 may further include one or more inertial motion sensors 131 configured to detect motion of the C-arm, without limitation, illustrated as disposed on support bases 103, but can be disposed on one or more locations on radiation shields 108 *a* and 108*b*, and/or one or more locations in C-arm 10.

System 110 may optionally include one or more operator detection sensors 161 configured to detect an intended or an actual operation (i.e., movement) of the C-arm 10. Operator detection sensors 161 is illustrated as disposed on and/or at one or more operative elements of control panel 11 of C-arm 10 and/or foot pedal 21 of C-arm 10. Various types of operator detection sensors 161 are contemplated such as proximity sensor, contact sensor, IR sensor, optic sensor.

Radiation shield operation control panel 111 which controls operation of system 100 (e.g., the extension and contraction of shields 108*a* and 108*b*) can be further equipped with one or more supplementary sensors (e.g., operator detection sensors 161, and electrical current sensor 151).

As described above, sensors 121, 131, 141, 151 and 161, may trigger native sensors 16 and/or the native anti-collision mechanism of C-arm 10, and/or communicate with a command controller 112 of supplementary radiation shielding apparatus 110. Command controller 112 is configured to receive signals detected by the supplemental sensors and can cooperate with/transmit signals to: i) one or more native sensors 16 of C-arm 10; ii) native anti-collision mechanism of C-arm 10; iii) an operation control unit of the C-arm 10 (e.g., controls movement of the C-arm; operation control unit of C-arm 10 is not shown); and/or iv) an operation control unit of the radiation shielding apparatus 100 (e.g., controls movement of radiation shields 108; operation control unit of apparatus 100 is not shown). Supplemental sensors may alternatively communicate directly with C-arm 10 or a portion thereof. For example, supplemental sensors may activate native anti-collision mechanism of C-arm 10 (optionally via a trigger mechanism, shown for example in 5-7), or communicate with an operation control unit of the C-arm 10 (e.g., controls movement of the C-arm).

Because radiation shields 108*a* and 108*b* and their support bases 103 are assembled around detector 12 and X-ray source 14, access to at least some native sensors 16 (FIG. 1) are partially or entirely limited or blocked, or otherwise interfered with. In order to mitigate collision risk, both the upper and lower radiation shields 108*a*, 108*b* are preferably significantly covered with sensors. These sensors include proximity 141 and/or contact sensors 121 (which may use capacitive sensing or any other type of proximity or contact sensor) and preferably face all possible collision directions (illustrated by arrows in FIG. 4). Inertial sensors 131 may be located almost anywhere on radiation shield apparatus 100 (e.g., upper and lower shields 108*a* and 108*b*) or on C-arm 10. Regardless, it may be preferable to attach inertial sensors 131 to upper shield 108*a* as it has two degrees of motion more than lower shield 108*b*.

In some cases, a potentially unsafe operation of C-arm 10 may be indicated via operator detection sensor 161, such as by way of foot-pedal 21 or other operator control mechanisms (e.g., a handle 19) on operation control panel 11, which may warrant cessation of operation of the C-arm, or which may operate native anti-collision mechanism of C-arm 10. An operator action (e.g., movement of C-arm via handle 19 or operating the C-arm's radiation emission via foot pedal 21) that may cause operator detection sensor 161 to trigger the C-arm's anti-collision means to cease movement thereof adds a further arrangement of protection for the C-arm 10 operation.

Figure 4:
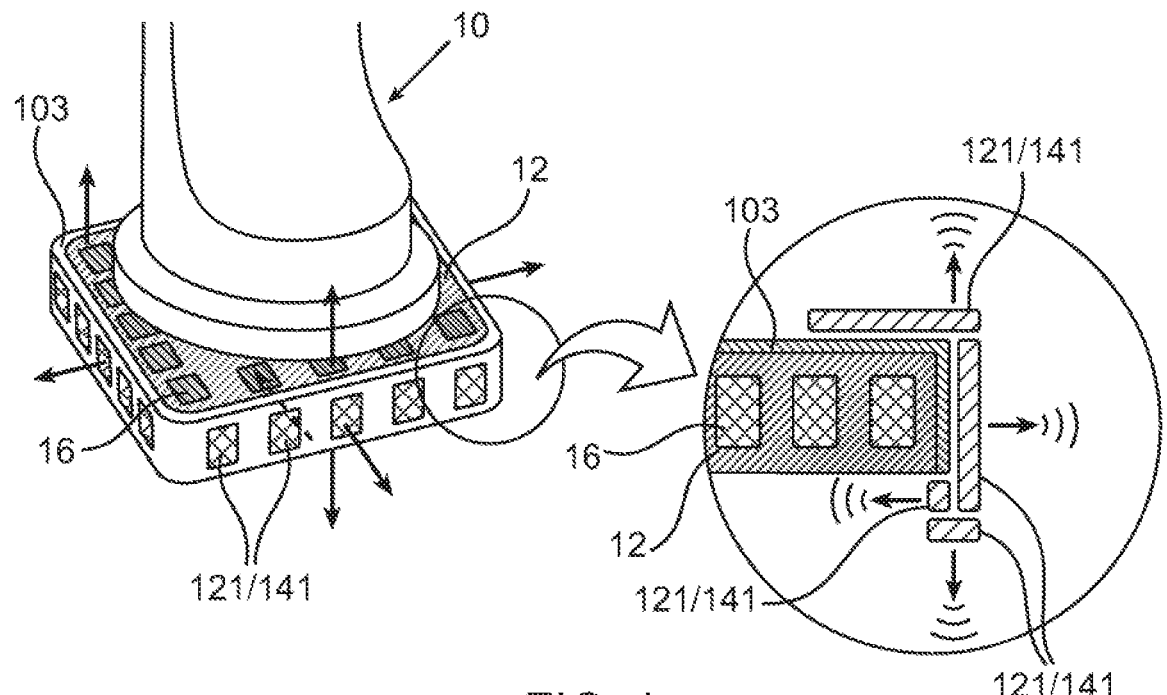
FIGS. 4 and 5 are perspective views of exemplary supplemental sensors of the present system.

FIG. 4 shows a plurality of supplemental sensors 121, 141 connected to one of the native sensors 16. As illustrated in the enlarged view of FIG. 4, supplemental sensors 121, 141 can be disposed facing all directions of potential collisions so as to provide a comprehensive detection of inappropriate proximity or contact with an entity, such as the patient or the X-ray table.

Figure 5:
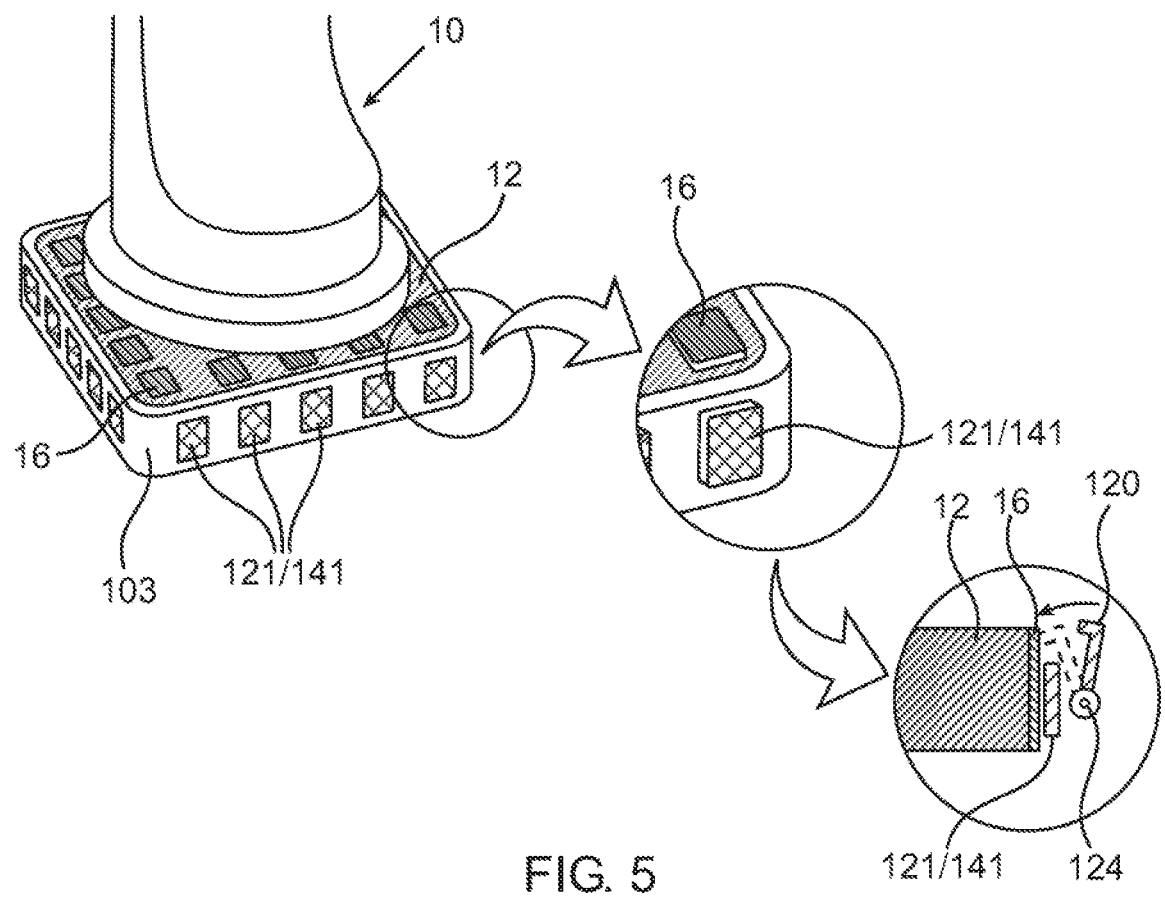

FIG. 5 illustrates a mechanical interface or trigger 120 configured to actuate the native anti-collision mechanism of C-arm 10, in particular one of the native sensors 16. An exemplary configuration of trigger 120 is shown, which is attached to or includes a trigger motor 124 (or other actuating mechanism). Trigger motor 124 is actuatable by supplemental sensor 121, 141 upon dangerous/inappropriate proximity or contact of radiation shield 108*a*, 108*b* or support base 103 with an entity, to interface (typically mechanically) with one of the native sensors 16. Trigger 120 is exemplified by an L-shaped member having a distal end, for example the short portion of the L-shaped member, configured to contact native sensor 16, upon actuation of the trigger 120. Trigger motor 124, in this design, is disposed at a proximal end of L-shaped trigger 120 and configured to receive a signal from supplemental sensor 121, 141 or from command controller 112 of radiation shielding apparatus 100 and to thereby pivot the trigger into contact with native sensor 16. Trigger motor 124 may also be configured to distance trigger 120 from native sensor 16 when the situation or threat of collision has passed. It should be understood that, depending on the operating circumstances, any of the sensors 121, 131, 141, 151 and 161 can activate trigger 120.

In the event of a potential collision of radiation shield 108*a*, 108*b* and/or support base 103 with an entity, proximity 141 and/or contact sensors 121 detect the potential collision (preferably prior to its occurrence), and physically mimics proximity or contact with detector 12 and/or X-ray source 14 of C-arm 10 in order to activate the existing/native anti-collision mechanism and particularly sensors 16. In some implementations, supplementary collision detection and prevention system 110 interfaces with the C-arm's software or electronics, to thereby trigger the native safety mechanism.

Supplemental sensors 121, 141, 131, 151, 161 for example those on radiation shields 108a, 108b, or on support base 103, or at the control panel 11, handle 19, or foot pedal 21, can actuate trigger motor 124 to cause trigger 120 to physically contact native sensor 16. Additionally, or alternatively, trigger 120 can operably interface with and thereby actuate native sensor 16 by other mechanisms, such as electrically or wirelessly; or mimic inappropriate proximity, in particular proximity closer than a threshold distance, and which may also take into account the velocity of the supplemental sensor in its approach to an entity. Thusly, trigger 120 actuates at least one C-arm native sensor 16, whereby the native anti-collision mechanism is activated. In accordance with some features, supplemental sensors 121, 141, 131, 151, 161 actuate one or more native sensors 16 (e.g. via trigger 120) through movement to a proximal location so as to cause one of the native sensors 16 to activate the native anti-collision mechanism.

Figure 6A:
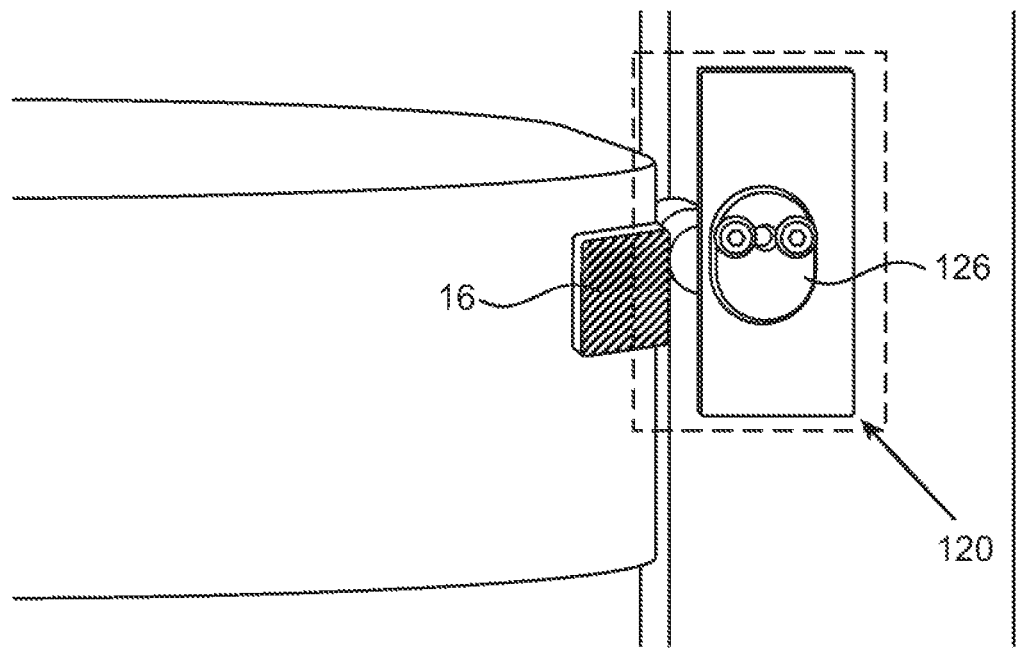
FIGS. 6A and 6B are schematic illustrations of an exemplary mechanical trigger mechanism of the present system, in a non-communicating/non-interfacing position (FIG. 6A); and a communicating/interfacing position (FIG. 6B), with a native anti-collision sensor.
Figure 6B:
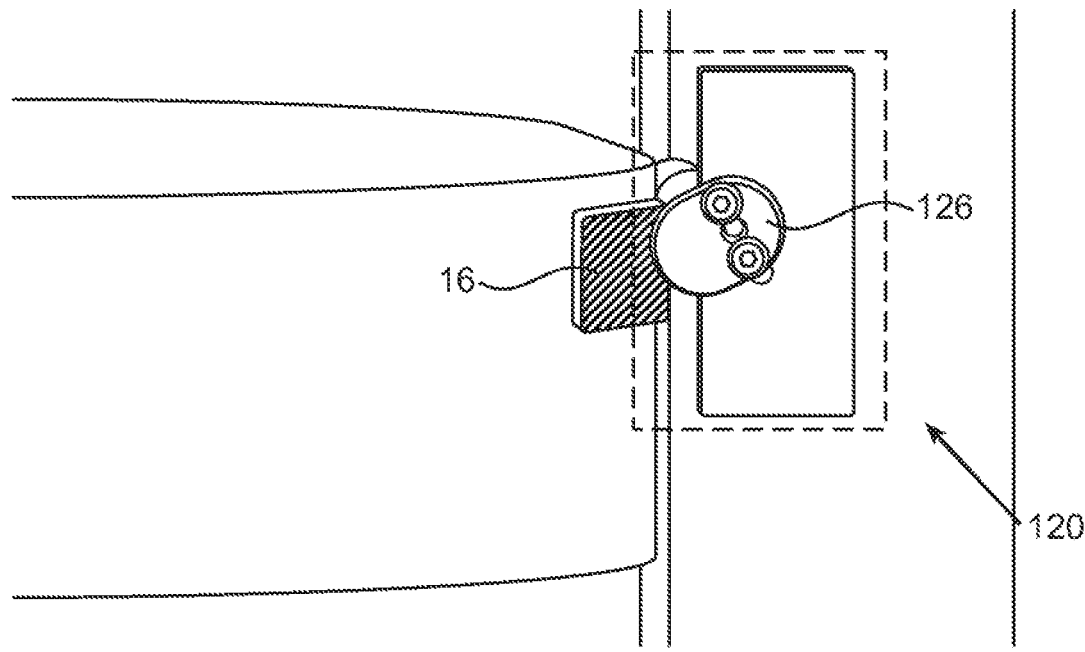

FIGS. 6A and 6B show another exemplary configuration of trigger 120 wherein the trigger has an oval or oblong-shaped trigger member 126 that can be rotated to interface with native sensor 16. In other words, based on a signal from the supplemental sensors 121 and/or 141, trigger 120 moves trigger member 126 to contact native sensor 16 or to mimic inappropriate proximity thereto by moving close to the native sensor.

FIG. 6A illustrates trigger 120 in a non-actuating state whereby the trigger does not trigger native sensor 16, indicating safe operation of C-arm 10. FIG. 6B illustrates trigger 120 in an actuating state whereby the trigger interfaces with native sensor 16, indicating an unsafe operation of C-arm 10 (e.g. undue proximity of radiation shield 108 with an entity, and/or contact therewith).

Figure 8:
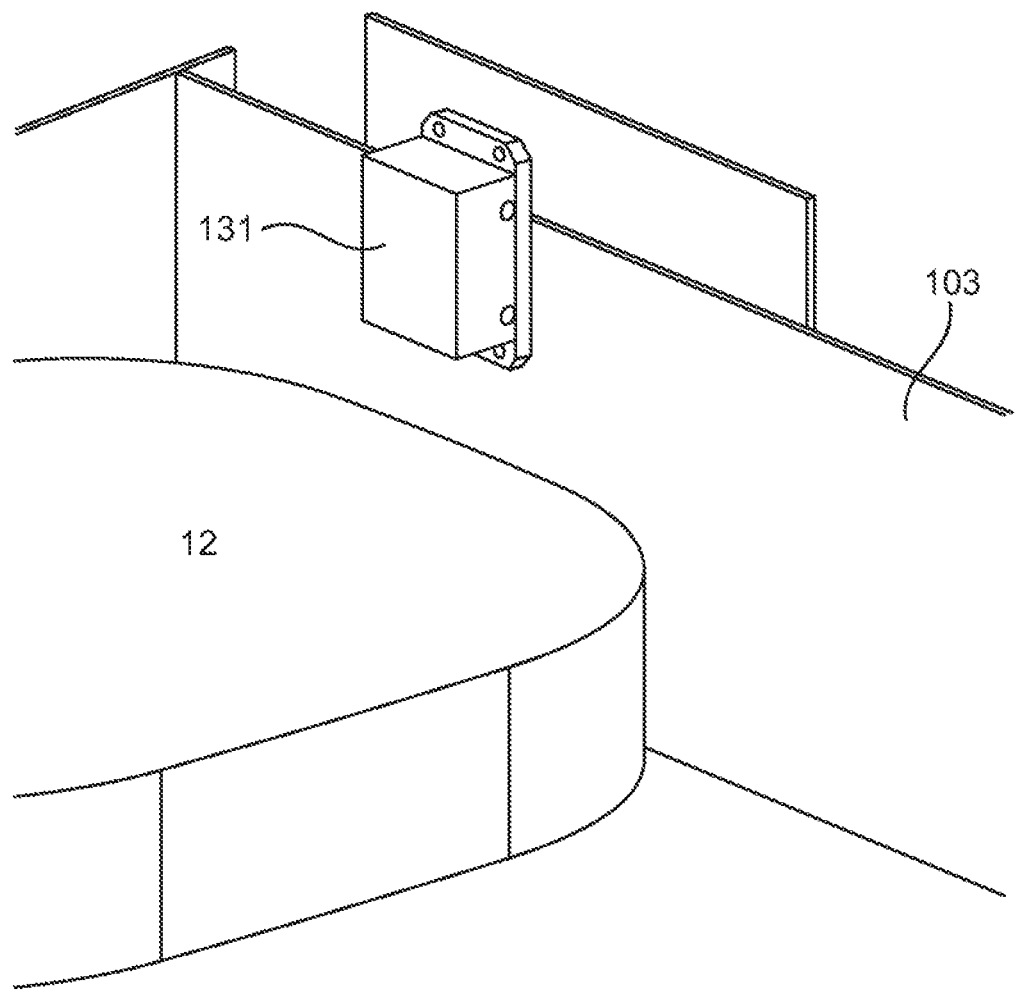
FIG. 8 is a schematic perspective view of an inertial motion sensor of the present system.

FIGS. 7A-7C depict yet another exemplary configuration of trigger 120 wherein trigger motor 124 rotates to move trigger 120 back and forth in a generally linear motion. In FIG. 7A, trigger 120 is rotated so that a trigger pin 128 is translated downward to interface (i.e. contact or mimic inappropriate proximity) with native sensor 16. FIGS. 7B and 7C show trigger 120 being operated so that a trigger pin holding element 130 is translated back and forth (upward and downward in the figures) so that trigger pin 128 is spaced-apart from a portion of native sensor 16 (FIG. 7B) and not actuating the native sensor; or in contact with the native sensor 16 (FIG. 7C) so as to actuate the native sensor. FIG. 8 shows an exemplary arrangement of inertial motion sensor 131 connected to support base 103 of radiation shielding apparatus 100 and/or connected to one or both of radiation shields 108a, 108b. Inertial motion sensor 131 is configured to sense an inappropriate or dangerous movement of radiation shields 108a, 108b and/or C-arm 10. For example, inertial motion sensor 131 may be coupled to one or more locations of support base 103 or radiation shields 108a, 108b of C-arm's detector 12. Inertial motion sensor 131 can be particularly useful in that it can aid in detecting movement/rotation of C-arm 10. If C-arm 10 is moving; accelerating or decelerating; or changing course/direction, this information can be used in an algorithm of command controller 112 of radiation shielding apparatus 100 to determine how quickly, if at all, to actuate native sensor 16. Inertial sensor 131 (like all of the supplemental sensors 121, 131, 141, 151, 161) can operably interface with the command controller 112 of apparatus 100 and upon inappropriate and/or unauthorized movement, the inertial sensor 131 sends feedback to the command controller 112 to activate the native anti-collision means of C-arm 10 (optionally via trigger 120). Alternatively, or additionally, inertial sensor 131 (like all of the supplemental sensors 121, 131, 141, 151, 161) when detecting inappropriate and/or unauthorized movement, may communicate directly and send feedback to the native anti-collision means of C-arm 10.

Figure 9:
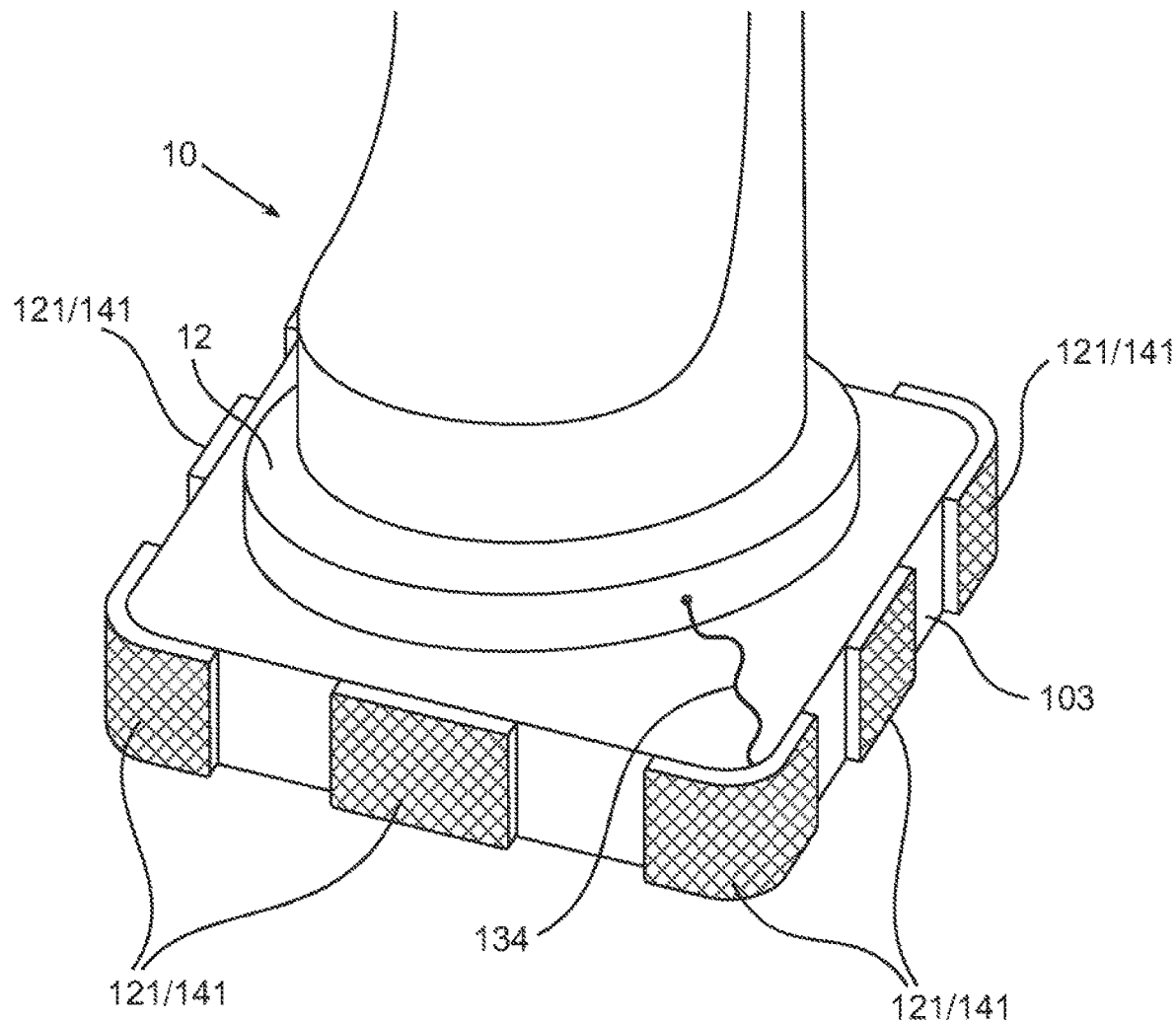
FIG. 9 is a perspective view of an operable connection of the present system to the C-arm and/or C-arm's native anti-collision means.

FIG. 9 illustrates contact sensor 121 and capacitive/proximity sensor 141 connected electrically, via to C-arm 10 via an interface (herein a wire or cable 134). The sensors 121 and 141 may communicate directly, i.e., without triggering trigger 120, with the C-arm native anti-collision mechanism. Sensors 121 and 141 may communicate with the anti-collision mechanism of the C-arm via an electrical and/or software interface that transmits a signal to actuate the native anti-collision mechanism.

Figure 10:
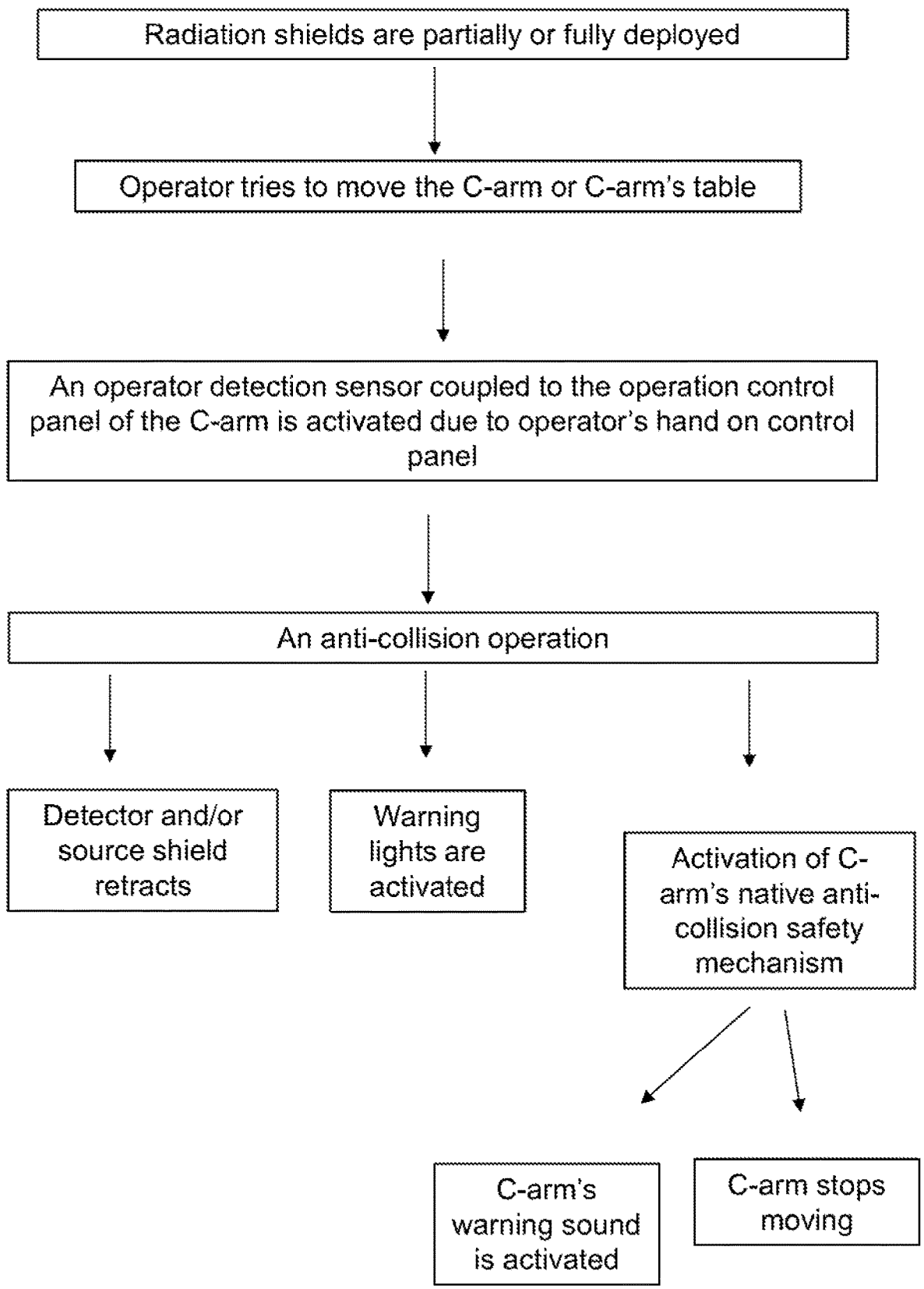
FIG. 10 is a flow chart depicting safety outcomes associated with activation of an operator detection sensor.

FIGS. 10-14 show flowcharts illustrating possible unsafe scenarios that may occur during X-ray imaging using a C-arm and further illustrate exemplary safety outcomes/steps when utilizing the present supplementary collision detection and FIG. 10 is a flow chart depicting a scenario where the shields 108a, 108b are fully deployed or are being deployed and the operator intends to move the C-arm or X-ray table. In order to move the table/C-arm, the operator typically manipulates the C-arm's operation control panel 11 and specifically handle 19. By doing so, operator detection sensor 161 (e.g., proximity or contact, sensor) coupled to handle 19 will sense the hand and then actuate an anti-collision operation of system 110. Optionally, a lower shield supplementary sensor is activated to thereby stop movement or avoid movement of the c-arm. Optionally, warning lights are operated. The native C-arm's anti-collision safety mechanism is activated, stimulating activation of C-arm's warning sound. C-arm 10 stops moving due to C-arm's native anti-collision safety mechanism activation. Operation may be continued when the sensors do not detect an entity in contact therewith or in proximity therewith or applying pressure on the sensors.

Figure 11:
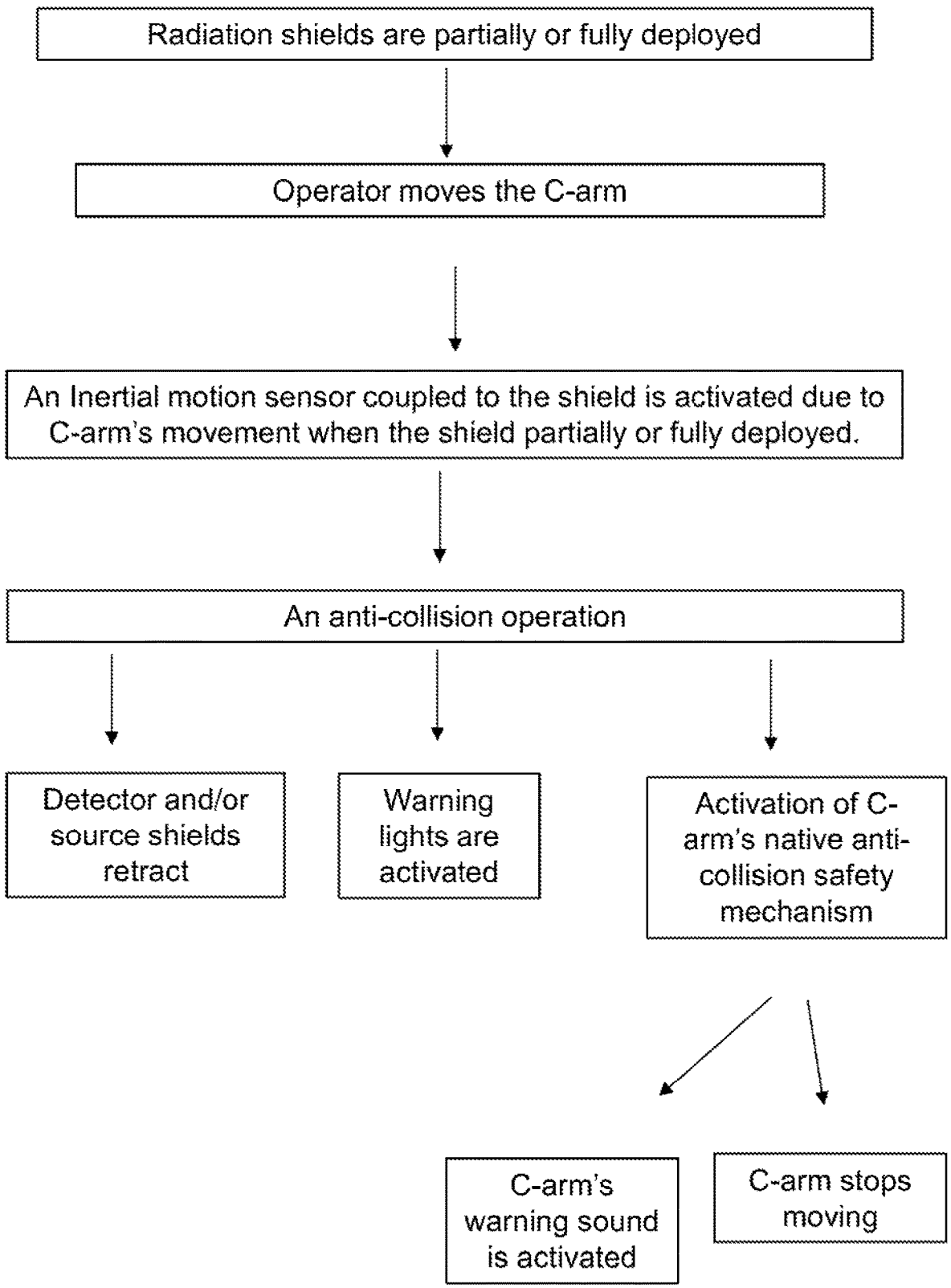
FIG. 11 is a flow chart depicting safety outcomes associated with an inertial motion sensor.

FIG. 11 is a flow chart depicting a scenario where the shields are partially or fully deployed, and the operator moves C-arm 10 or C-arm's table without fully retracting one or both shields 108a, 108b. Inertial motion sensors 131 coupled to one of shields 108a, 108b or support base 103 of the radiation shielding apparatus 100 detect movement of C-arm 10 when one or both shields 108a, 108b are in a partially extended position or in a fully extended position. This scenario illustrates a situation wherein operator detection sensor 161 is disabled. An anti-collision operation of system 110 is actuated. For example, a data from sensor 131 that motion has occurred when shields are deployed or partially deployed is transmitted to the command controller 112 that operates the native anti-collision means of C-arm 10 (optionally, via trigger 120) to stop movement of the C-arm. Command controller 112 may also transmit a command to retract shields 108a, 108b. Optionally, one or more sensors of lower shield is activated to thereby stop movement of the C-arm. Optionally, warning lights are operated. The native C-arm's anti-collision safety mechanism is activated stimulating activation of the C-arm's warning sound. Operation may be continued when the sensors do not detect an entity in contact therewith or in proximity therewith or applying pressure on the sensors.

Figure 12:
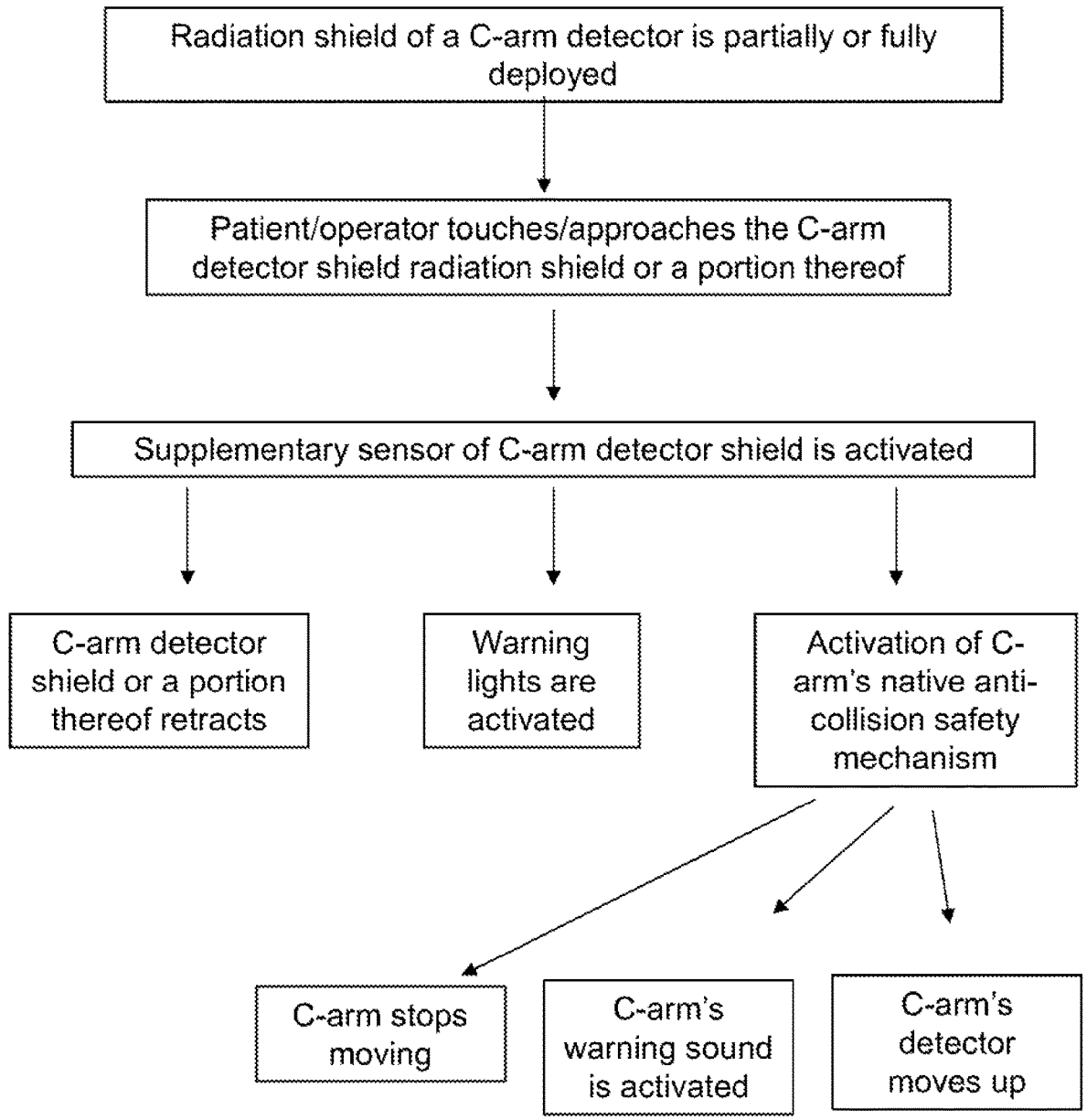
FIG. 12 is a flow chart depicting safety outcomes associated with imminent collision or collision of an entity with a radiation shield of a C-arm's detector.

FIG. 12 is a flow chart depicting a typical X-ray imaging procedure wherein a C-arm, such as C-arm 10, and a shielding apparatus, such as apparatus 100, is used. In such typical cases during the X-ray procedure, the radiation shields 108a, 108b are deployed or at least partially deployed. The flow chart depicts a situation wherein sensors 131 and 161 are disabled. An entity (e.g., a patient or an operator) touches or approaches upper radiation shield 108a, or a portion thereof (e.g., a segment of upper shield 108a, such as segment 107 (FIG. 2). As a result, one or more supplementary sensors of upper shield 108a (e.g. sensors 121, or 141) is activated, triggering retraction of upper shield 108a or a portion thereof (e.g., segments 107 associated with the imminent or actual collision). Optionally, activation of upper shield sensors includes operation of warning lights (not shown). The native C-arm's anti-collision safety mechanism is also activated, optionally by trigger 120, and/or by command controller 112, thereby activating C-arm's warning sound and retraction of detector 12 of the C-arm 10. Operation of C-arm 10 may be continued when the sensors do not detect an entity in contact with, or in close proximity to, or applying pressure on, the sensors.

Figure 13:
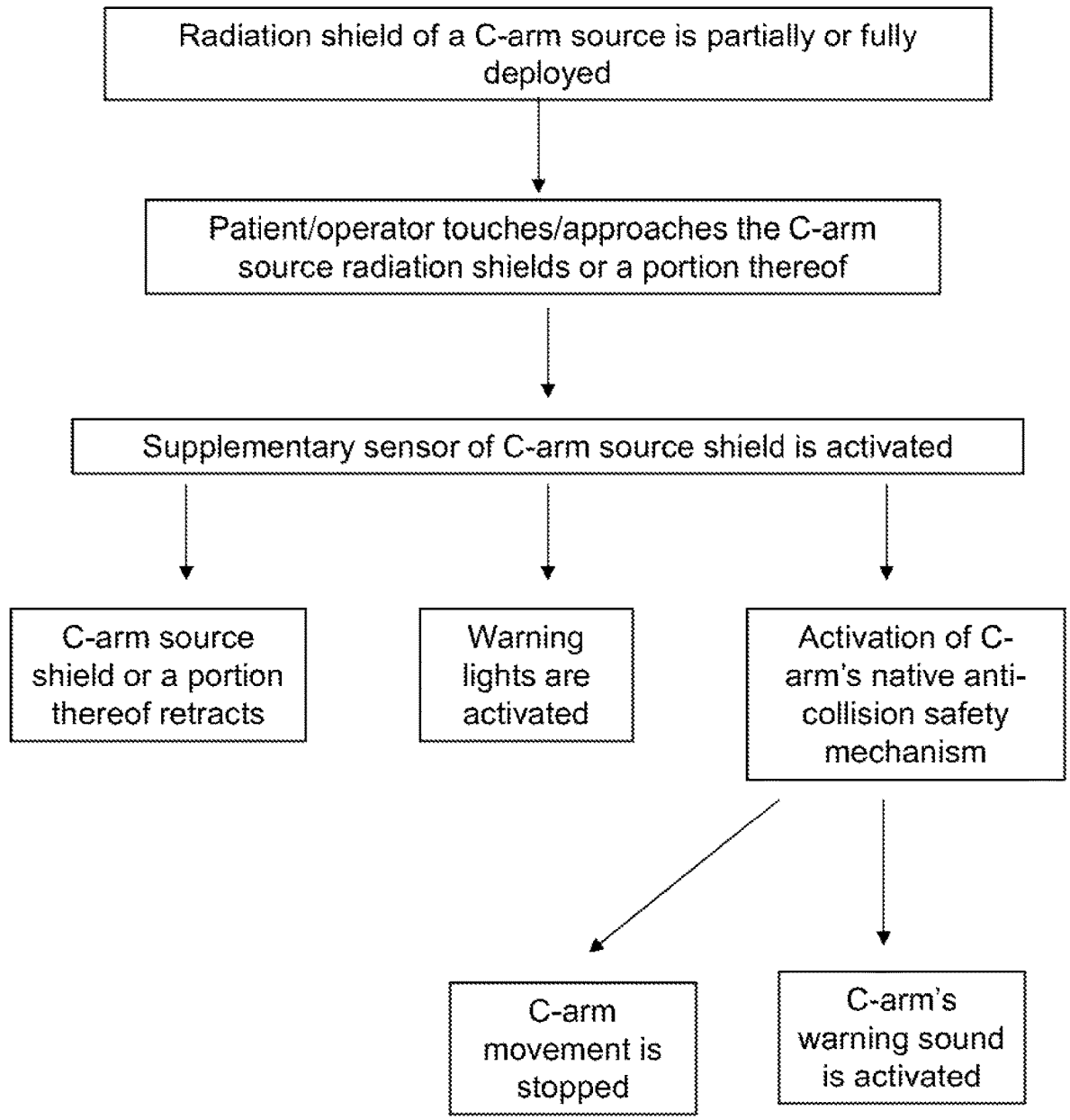
FIG. 13 is a flow chart depicting safety outcomes associated with collision or imminent collision of an entity with a radiation shield of a C-arm's X-ray source.

FIG. 13 is a flow chart depicting a typical imaging procedure wherein the lower radiation shield 108b is deployed or at least partially deployed and an entity (e.g., a patient or an operator) touches or approaches the lower radiation shield, or a portion thereof (e.g., a segment of lower shield 108b, such as segment 107—FIG. 2). The flow chart depicts a situation wherein sensors 131 and 161 are disabled. One or more supplementary sensors of lower shield 108b (e.g. sensors 121, 141) is activated, triggering retraction of the lower shield or a portion thereof (e.g., the segment(s) associated with the imminent or actual collision). Optionally, activation of lower shield sensors includes operation of warning lights. The native C-arm's anti-collision safety mechanism is further activated, optionally by trigger 120, and/or by command controller 112, activating C-arm's warning sound. Operation of C-arm 10 may be continued when the sensors do not detect an entity in contact with, or in close proximity to, or applying pressure on the sensors.

Figure 14:
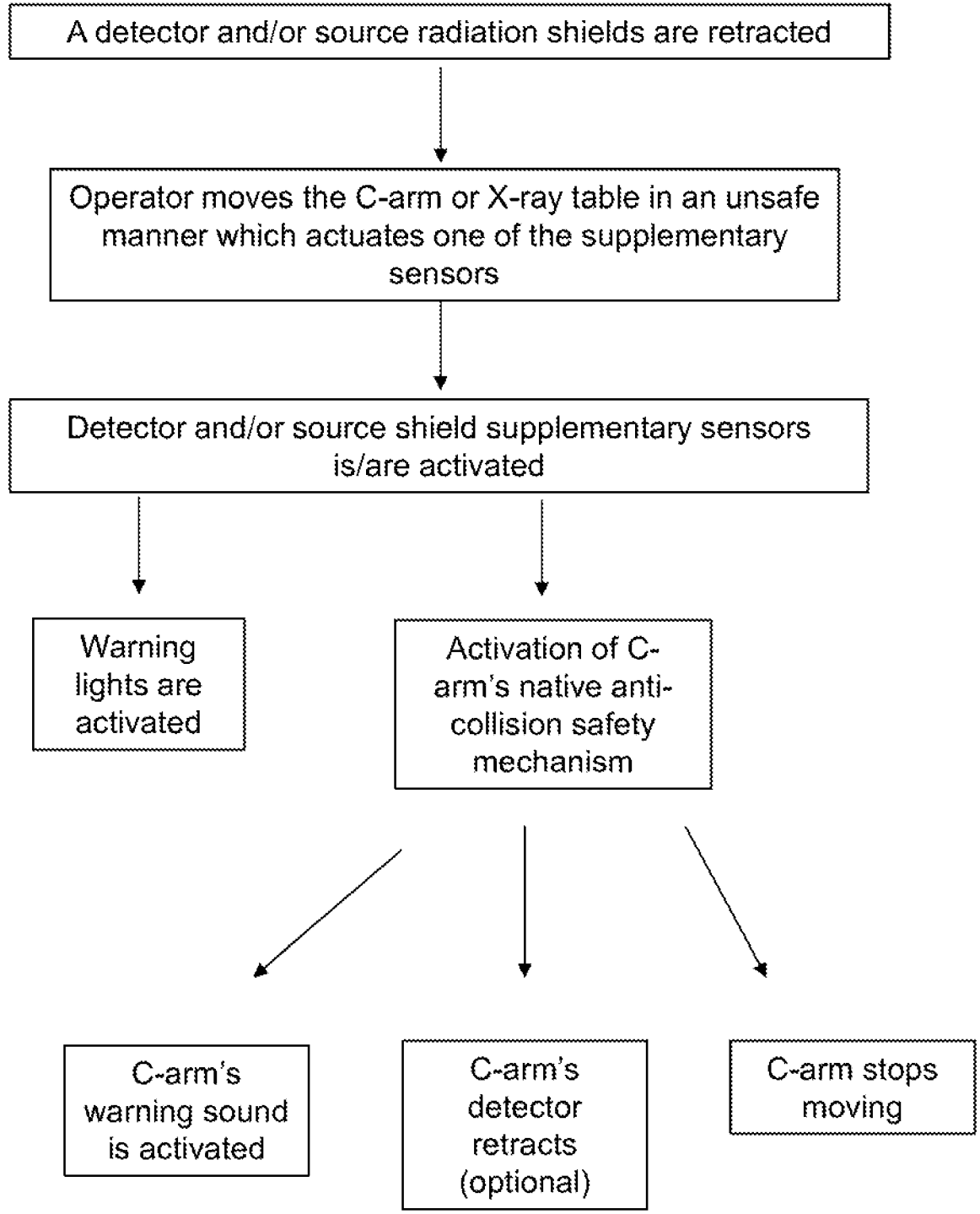
FIG. 14 is a flow chart depicting safety outcomes associated with collision or imminent collision of an entity with a C-arm, or a radiation shielding apparatus, or a portion thereof.

FIG. 14 is a flow chart depicting a scenario wherein radiation shield 108a and/or 108b is retracted and an operator moves C-arm 10 or the C-arm's table and touches or approaches the supplementary sensor(s), i.e., contact or proximity. The lower and/or upper supplementary sensors are activated, i.e., depending whether sensors of the upper or lower shield 108a, 108b are activated. Optionally, warning lights are operated. The native C-arm's anti-collision safety mechanism is activated, optionally by trigger 120, and/or by command controller 112, stimulating activation of C-arm's warning sound. C-arm 10 stops moving. Operation may be continued when the sensors do not detect an entity in contact therewith or in proximity therewith or applying pressure on the sensors.

Thus, as understood, when one of supplemental sensors 121, 131, 141, 151, or 161 detects a possible collision or detects a relevant operator activity, an interface may trigger the native anti-collision mechanism or procedure of C-arm 10 in order to stop its motion, warn the operator and/or prevent the collision. The interface may be a command controller 112 or may be a direct communication (via a wire, e.g., wire 134, or wireless) between the supplemental sensors and the native anti-collision mechanism of the C-arm.

In some implementations, one or more of the supplemental sensors 121, 131, 141, 151 and 161 surround certain portions of the C-arm 10, e.g. detector 12, collimator x-ray source 14. Optionally, supplemental sensors may be directed at sensing collisions of the C-arm 10 or a portion thereof and/or add-on systems to the C-arm. Thus, supplemental sensors may be mounted on X-ray equipment or an x-ray add-on system. For example, the additional sensors may be placed in one or more locations around and/or on the C-arm and/or parts thereof, e.g. surrounding the detector/image intensifier, surrounding the collimator/X-ray source, among other locations. Optionally, the additional sensor may be directed at sensing possible collisions in a range of at least about 90°, or at least about 180°, or more, or less, or a value in between. In an exemplary embodiment, one or more contact sensors 121 may be placed/mounted to one or more locations in support base 103 and/or radiation shield 108. In an exemplary embodiment, one or more proximity sensors 141 may be placed/mounted to one or more locations in support base 103 and/or radiation shield 108. In an exemplary embodiment, one or more inertial motion sensors 131 may be placed/mounted to one or more locations in support base 103 and/or radiation shield 108. In an exemplary embodiment, one or more electrical current sensors 151 may be placed/mounted to one or more locations in a motor or other locations in the C-arm to sense operation of a motor of the C-arm. In an exemplary embodiment, one or more inertial motion sensors 131 may be placed/mounted to one or more locations in support base 103 and/or radiation shield 108. In an exemplary embodiment, one or more operator detection sensors 161 may be placed/mounted to one or more locations in foot pedal 21 of C-arm 10. In an exemplary embodiment, one or more operator detection sensors 161 may be placed/mounted to one or more locations in operation control panel 11 of C-arm 10.

Supplemental sensors may be connected to an interface which actuates/mediates an anti-collision operation. The interface may further include a trigger mechanism (such as trigger 120) which, when operated, activates the X-ray equipment's anti-collision safety means. The interface may be a mechanical support structure mounted on or proximate to the X-ray equipment or add-on thereto. For example, the interface/mechanical support may be mounted on/proximate the detector or collimator of a C-arm. Alternatively, or additionally, the interface may be an electrical wire that communicates with the anti-collision safety mechanism or portion thereof (e.g., trigger 120). Alternatively, or additionally, the interface may be a command controller that communicates with the anti-collision safety mechanism (e.g., trigger 120).

Alternatively, or additionally, the sensor and/or trigger mechanism may be mounted directly onto X-ray equipment, without requiring any interface or a mechanical support structure. The trigger mechanism may include mechanical and/or an electrical activation means.

The actuation (e.g. trigger) can directly interface with a native sensor or position an element to set off the native sensor of the X-ray equipment. For example, a motor/actuator actuates an element detectable by the native sensor via applying pressure or contact or close proximity with the C-arm's native sensor.

Additionally or alternatively, the interface may interact directly with the native anti-collision mechanism (i.e. bypassing the C-arm's collision sensor 16). For example, an electrical trigger employs an electrical connection to C-arm 10 and/or portions thereof to activate the C-arm's anti-collision safety procedure. For example, activation may be by a direct electrical signal to the X-ray equipment's control system and/or electrical system.

The interface may include one or more triggers, placed in one or more locations around and/or on the X-ray equipment. For example, multiple triggers may be used to provide redundant protection (for example, if one of the sensors of the X-ray equipment connected to a mechanical trigger malfunctions, a second trigger may nevertheless trigger collision protection).

The interface may include a wireless connection to the X-ray native safety mechanism. For example, a remote sensor may be positioned on, near and/or directed toward a patient and/or a vulnerable piece of equipment that is not directly attached to a moving component (e.g. the C-arm, detector, collimator etc.). Optionally, when the supplemental sensor detects that the moving component is approaching a patient, an obstacle and/or the vulnerable object, the supplemental sensor sends a wireless signal to the interface which activates the collision prevention system of the X-ray system. For example, a remote sensor may include a proximity sensor, and/or a contact and/or a pressure sensor and/or a strain sensor and/or a thermal sensor, etc., as noted above, for detecting proximity and/or contact of the X-ray device with the patient, an obstacle and/or vulnerable objects. Alternatively, or additionally, a remote supplemental sensor may include visual or optical means (e.g. a video camera and/or a laser and/or radar and/or the like) directed at a sensitive location to detect when the X-ray equipment enters and/or approaches a sensitive area. Alternatively, or additionally, a remote sensor may be connected by hard wiring to an interface.

The present supplementary collision detection and prevention system 110 may cease activating the C-arm's native collision safety means when there is an indication that the potential or actual collision has ceased, and it is safe to maneuver the C-arm and/or components thereof and/or an add-on apparatus, such as a radiation shield. For example, the supplementary system may cease to activate the C-arm's native collision safety mechanism when the patient, table or other objects are no longer detected by the supplementary system's sensors. Ceasing activation of the C-arm's native collision safety means and/or operation may include retracting a mechanical trigger such that it no longer interfaces with (contacts, applies pressure to, is disposed in proximity to) the C-arm's native anti-collision safety sensors. Alternatively, or additionally, ceasing activation of the C-arm's native collision safety mechanism and/or operation may include sending a direct electrical signal to the C-arm and/or its control and/or electrical system.

Additionally or alternatively, supplementary collision detection and prevention system 110 may be a stand-alone system or may be integrated into C-arm 10 or may be part of radiation shielding apparatus 100 or may be part of a different system that is either stand-alone or integrated with the C-arm. Supplementary collision detection and prevention system 110 may act as an accessory or as an auxiliary system of a C-arm and may be a stand-alone system or may be partially or entirely integrated with a C-arm system or with a radiation shielding apparatus.

The supplemental sensors may duplicate the job of the native sensors and/or they may be disposed beyond the native sensor, e.g. covering a space not covered by the native sensor and/or the supplemental sensors may use a technology differing from the native sensors. Optionally, the supplemental sensors may be used to back-up the existing or native sensors. Optionally, the additional/supplemental sensors back up the existing or native sensors in cases where the collision safety mechanism of the X-ray equipment is inaccessible, obscured, inactive and/or does not operate properly.

Various positions of the additional collision sensor(s), actuator and/or mechanical trigger on the X-ray device may be implemented. Optionally or additionally, the position of the supplementary collision sensor(s), actuator and/or mechanical trigger on the X-ray device dictates the direction of collision prevention. For example, when the additional/supplemental sensor is on the right side of the detection prevention mechanism/X-ray device, the actuator may actuate a native collision sensor on the right side, e.g. to cause a collision avoidance of a collision from the right side.

Each of the following terms: 'includes', 'including', 'has', 'having', 'comprises', and 'comprising', and, their linguistic, as used herein, means 'including, but not limited to', and is to be taken as specifying the stated component(s), feature(s), characteristic(s), parameter(s), integer(s), or step (s), and does not preclude addition of one or more additional component(s), feature(s), characteristic(s), parameter(s), integer(s), step(s), or groups thereof.

Each of the phrases 'consisting of' and 'consists of', as used herein, means 'including and limited to'.

The term 'consisting essentially of' as used herein means that the scope of the claim is limited to the specified elements and those that do not materially affect the basic and novel characteristic(s) of the claimed device and materials.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably.

The term 'about', is some embodiments, refers to ±30% of the stated numerical value. In further embodiments, the term refers to ±20% of the stated numerical value. In yet further embodiments, the term refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub combination in the context or format of a single embodiment, may also be illustratively described and presented in the context or format of a plurality of separate embodiments.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A supplementary collision detection and prevention system for use in combination with medical imaging equipment which includes a native anti-collision mechanism having native sensors and an add-on system that limits a functionality of the native anti-collision mechanism, the supplementary collision detection and prevention system comprising:
    a plurality of supplemental sensors incorporated into the add-on system and being any one of a proximity sensor and/or contact sensor, and/or an inertial motion sensor, and/or an operator detection sensor, and/or an electrical current sensor configured to facilitate prevention or protection from collision with an entity; and
    an interface configured to receive communication from at least one of the plurality of supplemental sensors and to transmit a signal to the native anti-collision mechanism to actuate an anti-collision operation of the medical imaging equipment to avoid or mitigate a collision.

2. The system of claim 1, further comprising a command controller configured to actuate the anti-collision operation of the medical imaging equipment.

3. The system of claim 1, wherein the add-on system is a radiation blocking shield and wherein at least one of the supplemental sensors is associated with the radiation blocking shield.

4. The system of claim 1, wherein at least one of the plurality of supplemental sensors is selected from the group consisting of: a pressure sensor; a strain sensor; an infrared sensor; an ultrasonic sensor; an ultrasound sensor; a laser sensor; a radio frequency sensor; an electro-optic sensor; and a thermal sensor, or any combination thereof.

5. The system of claim 1, wherein the electrical current sensor is configured to measure electrical current consumption in one more units of the medical imaging equipment and detect operation thereof that may lead to collision with the entity.

6. The system of claim 1, wherein the operator detection sensor is configured to detect an activity by an operator that can lead to collision with the entity.

7. The system of claim 1, wherein the operator detection sensor is associated with a foot pedal or an operation control panel of the medical imaging equipment.

8. The system of claim 1, wherein the operator detection sensor is selected from the group consisting of a proximity sensor; a contact sensor; an infra-red sensor; an optic sensor; or a combination thereof.

9. The system of claim 1, wherein the inertial motion sensor is an accelerometer or a gyroscopic sensor.

10. The system of claim 1, wherein the inertial motion sensor is configured to detect movement of a moving part of the medical imaging equipment.

11. The system of claim 1, wherein the entity is a patient, a patient table, an operator or a piece of medical imaging equipment.

12. The system of claim 3, wherein the radiation blocking shield extends from a radiation shield support base and wherein said support base includes one or more of the plurality of supplemental sensors.

13. The system of claim 3, wherein the radiation shield is a retractable shield that is configured to retract in response to said signal.

14. A radiation shielding system comprising:
    (a) at least one radiation blocking shield configured to be positioned around an X-ray source or an X-ray detector of a medical imaging equipment;
    wherein the medical imaging equipment includes a native anti-collision detection mechanism including at least one native sensor;
    (b) a supplementary collision detection and prevention system configured to avoid collision of an entity with the X-ray source and/or X-ray detector of the medical imaging equipment, the supplementary collision detection and prevention system including a plurality of supplemental sensors being any one of a proximity sensor and/or contact sensor, and/or an inertial motion sensor, and/or an operator detection sensor, and/or an electrical current sensor configured to facilitate prevention or protection from collision with said entity; and
    (c) a command controller configured to receive communication from the supplemental sensors and mechanically and/or electrically actuate an anti-collision operation of the medical imaging equipment to avoid or mitigate a collision; and
    a mechanical trigger configured to actuate at least one of the native sensors in response to said mechanical and/or electrical operation, thereby activating the native anti-collision mechanism of the medical imaging equipment.

15. The system of claim 14, wherein said electrical anti-collision operation includes an electrical trigger that actuates the native anti-collision mechanism.

16. The system of claim 14, wherein at least one of the supplemental sensors is associated with the radiation blocking shield.

17. The system of claim 14, wherein the radiation blocking shield includes a radiation shield support base, further comprising one or more of the supplemental sensors mounted on said radiation shield support base.

18. The system of claim 14, wherein at least one of the supplemental sensors is a sensor selected from the group consisting of: a pressure sensor; a strain sensor; an infrared sensor; an ultrasonic sensor; an ultrasound sensor; a laser sensor; a radio frequency sensor; an electro-optic sensor; and a thermal sensor, or any combination thereof.

19. The system of claim 14, wherein the electrical current sensor is configured to measure electrical current consumption in one or more units of the medical imaging equipment and detect operation thereof that may lead to collision with the entity.

20. The system of claim 14, wherein the operator detection sensor is configured to detect an activity by an operator that can lead to collision with the entity.

21. The system of claim 14, wherein the operator detection sensor is associated with a foot pedal or an operation control panel of the medical imaging equipment.

22. The system of claim 14, wherein the operator detection sensor is selected from the group consisting of a proximity sensor; a contact sensor; an infra-red sensor; an optic sensor; or a combination thereof.

23. The system of claim 14, wherein the inertial motion sensor is a gyroscopic sensor.

24. The system of claim 14, wherein the inertial motion sensor is disposed on the radiation blocking shield, and/or the X-ray source and/or the X-ray detector.

25. The system of claim 14, wherein the entity is a patient, a patient table, an operator or a piece of C-arm equipment.

26. A method of detecting and/or avoiding a collision between (a) a moveable portion of a piece of medical imaging equipment and (b) an entity, wherein the medical imaging equipment includes a native anti-collision mechanism, the method comprising:

placing a radiation blocking shield over at least a portion of the medical imaging equipment, wherein the native anti-collision mechanism includes native anti-collision sensors and wherein the radiation blocking shield limits a functionality of the native anti-collision sensors of the native anti-collision mechanism;

arranging of a plurality of supplemental sensors on the radiation blocking shield;

sensing with the plurality of supplemental sensors proximity and/or contact between the entity and the moveable portion of a piece of medical imaging equipment;

communicating the sensing of such proximity and/or contact between the entity and the moveable portion to a command controller of the radiation blocking shield; and mechanically and/or electrically actuating an anti-collision operation of the medical imaging equipment to avoid or mitigate a collision between the entity and the moveable portion.

27. The method of claim 26, further comprising mechanically triggering at least one of the native sensors in response to said mechanical and/or electrical operation.

28. The method of claim 26, further comprising transmitting a signal to an electrical trigger that actuates the native anti-collision mechanism.

29. The method of claim 26, wherein actuating the anti-collision operation comprises retracting the radiation blocking shield.

30. The method of claim 26, further comprising stopping or slowing the moveable portion of the medical imaging equipment.

* * * * *